(12) United States Patent
Barrientos et al.

(10) Patent No.: US 12,350,180 B2
(45) Date of Patent: Jul. 8, 2025

(54) SHOULDER IMMOBILIZER AND ARM APPARATUS

(71) Applicant: OSSUR ICELAND EHF, Reykjavik (IS)

(72) Inventors: Matthew Barrientos, Foothill Ranch, CA (US); Mark Harman Powell, Foothill Ranch, CA (US); Asdis Bjornsson, Foothill Ranch, CA (US); Jane Price, Foothill Ranch, CA (US); Eugenio Luna, Foothill Ranch, CA (US)

(73) Assignee: OSSUR ICELAND EHF, Reykjavik (IS)

( * ) Notice: Subject to any disclaimer, the term of this patent is extended or adjusted under 35 U.S.C. 154(b) by 170 days.

(21) Appl. No.: 17/768,991

(22) PCT Filed: Oct. 22, 2020

(86) PCT No.: PCT/US2020/056810
§ 371 (c)(1),
(2) Date: Apr. 14, 2022

(87) PCT Pub. No.: WO2021/081173
PCT Pub. Date: Apr. 29, 2021

(65) Prior Publication Data
US 2024/0099870 A1    Mar. 28, 2024

Related U.S. Application Data

(60) Provisional application No. 62/925,057, filed on Oct. 23, 2019.

(51) Int. Cl.
A61F 5/37    (2006.01)
A61F 5/01    (2006.01)

(52) U.S. Cl.
CPC ............ A61F 5/0118 (2013.01); A61F 5/373 (2013.01); A61F 5/3738 (2013.01)

(58) Field of Classification Search
CPC ........ A61F 5/0118; A61F 5/013; A61F 5/373; A61F 5/3723; A61F 5/3738;
(Continued)

(56) References Cited

U.S. PATENT DOCUMENTS 114,615 A     5/1871  Smitley
3,780,729 A  12/1973  Garnett
(Continued)

FOREIGN PATENT DOCUMENTS

DE    20116743 U    1/2002
EP    1013248 A1    6/2000
(Continued)

OTHER PUBLICATIONS

International Search Report and Written Opinion from Corresponding PCT Application No. PCT/US2020/056810, Feb. 16, 2021.

Primary Examiner — Victoria Hicks Fisher
(74) Attorney, Agent, or Firm — Workman Nydegger

(57) ABSTRACT

A shoulder immobilizer and arm apparatus are provided for enhanced comfort and ease of use for rehabilitating a shoulder. The shoulder immobilizer includes a double figure-9 strap configuration to support the weight of an injured arm and shoulder comfortably. The shoulder immobilizer can be stepped down for modular construction and use depending on a user's needs. The shoulder immobilizer may be configured to cooperate with a corresponding arm apparatus, including an open-frame sling allowing for elbow extension and a simplified strap configuration.

20 Claims, 14 Drawing Sheets

(58) Field of Classification Search
CPC .... A61F 5/3746; A61F 5/3753; A61F 5/3715; A61F 5/05858; A61F 5/01; A61F 5/0102; A61F 5/0104; A61F 5/37; A61F 5/40; A61F 5/058

See application file for complete search history.

(56) References Cited

U.S. PATENT DOCUMENTS

| | | |
|---|---|---|
| 4,487,199 A | 12/1984 | Saringer |
| 4,497,316 A | 2/1985 | Lilla |
| 4,598,702 A | 7/1986 | Lilla |
| 4,836,195 A | 6/1989 | Berrehail |
| 5,385,536 A | 1/1995 | Burkhead et al. |
| 5,407,420 A | 4/1995 | Bastyr et al. |
| 5,423,333 A | 6/1995 | Jensen et al. |
| 5,665,058 A | 9/1997 | Young |
| 6,862,870 B1 | 3/2005 | Coons |
| 7,563,236 B2 | 7/2009 | Kazmierczak et al. |
| 8,016,780 B1 | 9/2011 | Sickles |
| 8,109,273 B2 | 2/2012 | Golden et al. |
| 8,273,041 B2 | 9/2012 | Goumas |
| 8,454,544 B2 | 6/2013 | Barnes et al. |
| 9,492,303 B2 | 11/2016 | Golden et al. |
| 9,700,453 B2 | 7/2017 | Benenati |
| 9,827,133 B1 | 11/2017 | Krenzel |
| 9,968,477 B2 | 5/2018 | Lo |
| 10,143,270 B2 | 12/2018 | Fiedler et al. |
| 10,231,862 B2 | 3/2019 | Summit et al. |
| 10,285,841 B2 | 5/2019 | Pappady |
| 10,736,767 B2 | 8/2020 | Boileau et al. |
| 2003/0187373 A1 | 10/2003 | Gaylord |
| 2005/0010147 A1 | 1/2005 | Kazmierczak et al. |
| 2006/0258966 A1 | 11/2006 | Hargrave et al. |
| 2009/0192424 A1 | 7/2009 | Choudhury et al. |
| 2010/0152635 A1 | 6/2010 | Borden |
| 2012/0101421 A1 | 4/2012 | Albrecht |
| 2012/0245498 A1 | 9/2012 | Krenzel |
| 2013/0317401 A1 | 11/2013 | Joslin |
| 2014/0194798 A1 | 7/2014 | Sotereanos et al. |
| 2014/0221888 A1 | 8/2014 | Benenati |
| 2014/0371644 A1 | 12/2014 | Erbe et al. |
| 2015/0135486 A1 | 5/2015 | Fiedler et al. |
| 2016/0256311 A1 | 9/2016 | Lemmon et al. |
| 2017/0027737 A1 | 2/2017 | Boileau et al. |
| 2017/0042721 A1 | 2/2017 | Golden et al. |
| 2020/0253776 A1 | 8/2020 | Boileau et al. |
| 2020/0306072 A1* | 10/2020 | Carney ................ A61F 5/0102 |

FOREIGN PATENT DOCUMENTS

| | | |
|---|---|---|
| EP | 2833754 B1 | 4/2016 |
| EP | 3108859 A1 | 12/2016 |
| ES | 2734679 T3 | 12/2019 |
| JP | 2005245611 A | 9/2005 |
| JP | 6376930 B2 | 8/2018 |
| WO | 2019020960 A1 | 1/2019 |

\* cited by examiner

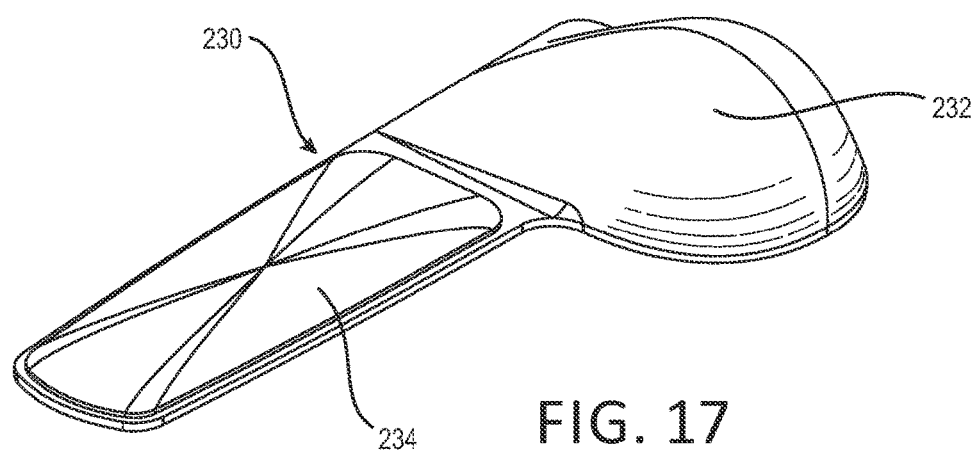
FIG. 17
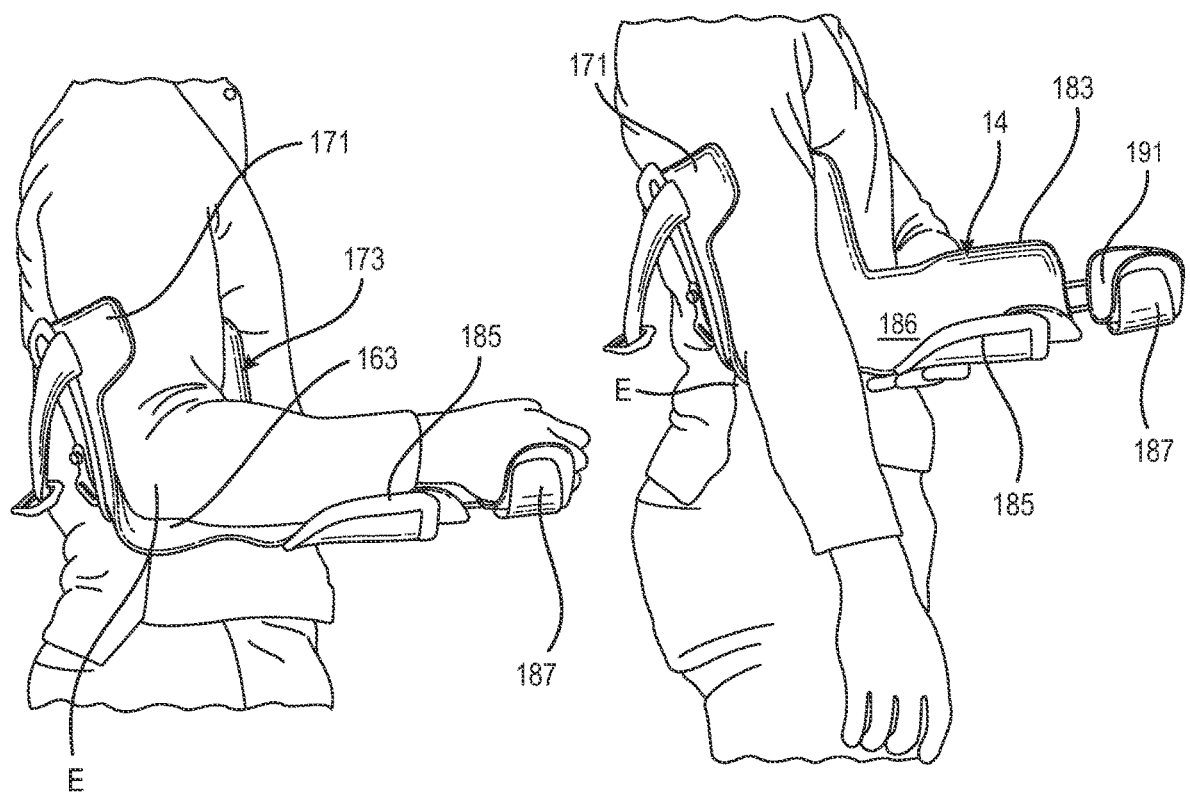
FIG. 17A
FIG. 17B

SHOULDER IMMOBILIZER AND ARM APPARATUS

FIELD OF THE DISCLOSURE

The disclosure relates to a shoulder immobilizer and arm apparatus for post-operative use or post-injury range of motion restriction at the shoulder.

BACKGROUND

After shoulder surgery, a shoulder is often placed in an immobilizer or sling for bracing and immobilization. The immobilizer is used to limit the motion of the shoulder so the recovering shoulder can heal. The immobilizer is often prescribed for a recovery period of four to six weeks after surgery. During this recovery time, there should be no reaching, lifting, pushing, or pulling of the recovering shoulder during this recovery period. During recovery, the individual may remove their arm of the recovering shoulder from the sling to bend and straighten their elbow to perform, for example, elbow range of motion, bathing, and dressing.

Known solutions for bracing and immobilization present a few problems. Many immobilizers are challenging to use, both for clinicians to fit the user initially and repetitively and for users to wear or adjust the immobilizer at home. Donning may be difficult on an unconscious user on an operating room bed, as often needs to be done immediately following a shoulder operation.

Users may complain of pain at their elbow or neck and sustained elbow stiffness or ulnar nerve pain. Many existing shoulder-immobilization solutions are anchored about the user's neck. Users frequently don the immobilizer at home while their shoulder is healing. Still, shoulder-immobilization solutions do not lend themselves to a simple, intuitive, and repeatable donning procedure, particularly with only one healthy shoulder. One reason is the complexity of existing shoulder immobilizers that require many straps that, to a user, mostly look the same and attach in similar ways, making it difficult for the user to understand how to don and doff the shoulder immobilizer at home properly. These straps may incur inadvertent securement to the sling or other straps, thereby inhibiting easy donning and doffing, and overcomplicating the immobilizer.

These same users often have difficulty with their shoulder immobilization while sleeping, as the immobilizers lack flexibility for the user to position their shoulder in bed comfortably. For instance, existing shoulder immobilizers often position the user's arm in a way that inhibits circulation, requiring users to lay their arm on a pillow or across the chest to prevent the arm from going numb. Unfortunately, this solution may not be ideal from a shoulder-immobilization perspective.

Current immobilizers may not be comfortable for the user, leading to user non-compliance, and lack versatility for moving the elbow during recovery of the corresponding shoulder. These current solutions are often simple to use but cheap and uncomfortable resulting in lower reimbursement for a clinician or bulky and overcomplicated, leading to a higher reimbursement for a clinician. The prescribed shoulder immobilizer may not well serve, either way, the user's needs, and dimensions. Further, the user's noncompliant use of the immobilizer can lead to longer recovery time and additional visits to the clinic, adding cost to the user's recovery.

The shoulder may be a complicated joint to stabilize comfortably. As clinicians prefer the shoulder to be abducted for a period of often three to six weeks, a solution that comfortably achieves sustained and proper use is desirable for recovery from surgical operations such as rotator cuff surgery, shoulder instabilities, and soft tissue repairs or strains. Another desirable quality in a shoulder immobilizer is providing a clinician the ability to adapt the immobilizer to different protocols and flexibility to adapt the immobilizer for various treatments. Examples of the flexibility of donning, an adaptation of protocols, and sustained use are desirable for pre-operative and operating room situations and users' ability to fit and wear the immobilizer correctly at home. For instance, a user may need various levels of immobilization at various stages of the day or different recovery stages, calling for a solution adaptable to a user's dynamic needs and dimensions.

There is a need for an intuitive and comfortable shoulder immobilizer that is easier to use and wear relative to current solutions and adaptable for a spectrum of treatment stages and different recovery protocols in a comfortable, proper, and intuitive manner.

SUMMARY

According to shoulder immobilizer and arm apparatus embodiments described, such embodiments are intuitive and comfortable to use and wear. The embodiments offer a modular construction that enables a clinician to step-down treatment options depending on the user's rehabilitation protocol. For example, the modular construction of a shoulder immobilizer and a separate but connectable arm apparatus allows the shoulder immobilizer to be stepped-down to a regular shoulder immobilizer instead of an abduction shoulder brace.

The arm apparatus is configured as an "open-frame" sling, meaning it can be modified with at least one enclosed loop to function as a conventional arm sling. The arm apparatus is preferably provided in the open-frame configuration to offer support combined with breathability and flexibility of use. The arm apparatus has formable cuffs for customized fit and support of the arm in abduction or neutral configurations. The open-frame configuration allows for elbow extension with ease. It offers a simple strap configuration enabling "quick fit" at designated locations to assure proper fit, with coded combinations, such as by color or indicia, to prevent attachment to wrong spots. A user and/or clinician is thereby guided to don the shoulder immobilizer and arm apparatus properly. The arm apparatus has clearances and surface reliefs or contours to enable easy donning and doffing without raising pressure points on the arm.

The shoulder immobilizer is arranged as a "double figure-9" strap configuration that comfortably supports the weight of the injured arm and/or shoulder. It can be modified by stepping down or stepping up, according to protocol, to a soft fabric sling or be combined with a more substantial mechanical apparatus depending on rehabilitation protocol. The double figure-9 strap configuration is unique from other strapping methods because it evenly distributes a load around the uninjured shoulder joint and distributes the load effectively between the hips and uninjured shoulder.

Traditional slings react or situate the load entirely on the neck. Other "gunslinger" sling designs attempt to offload the neck pressure with a secondary axillary strap that extends underneath the arm but relocates pressure to the axilla to do so. When the double figure-9 strap configuration is properly adjusted with equal tension, four straps associated with the double figure-9 strap configuration prevent an overall arm loop formed by such straps from sliding into or toward the neck and from sliding up into or toward the axilla. Each of the four straps counteracts one another to create a stabilized arm loop system. The tension is to be dialed in, and the strap configuration preferably offers repeatable tension because any loose strap will imbalance the system, causing comfort issues.

According to a preferred embodiment, anterior or front and posterior or back straps and portions are arranged at the same height on a user's body. Depending on the body type of the user, the height of these connection points may be adjusted. The tension is to be adjusted to keep the shoulder-immobilization system in balance. The counteracting strap tension stabilizes the injured arm in internal/external rotation. In embodiments, the strap tension can be intentionally biased to create internal/external rotation.

Combined with the strap configuration, the shoulder immobilizer is arranged for ergonomic donning using only the unaffected arm. The shoulder immobilizer has a simplified belt mechanism employing magnets to limit adjustment with preferably only the unaffected arm. To eliminate confusion when arranging straps, couplers and attachments are colored and sized differently to assure corresponding components are used with each other. Straps may be adjusted about the anterior or posterior according to chest geometry and held in place with a mechanical locking system permitting yet further simplified adjustment.

These and other features of the present disclosure will become better understood regarding the following description, appended claims, and accompanying drawings.

BRIEF DESCRIPTION OF THE DRAWINGS

FIG. 17 is a perspective view of an extension pad in the arm apparatus of FIG. 11.

FIG. 17A is a schematic view of an arm in the arm apparatus of FIG. 11 with a user's elbow in flexion.

FIG. 17B is a schematic view of an arm in the arm apparatus of FIG. 11 with a user's elbow in extension.

Figure 1:
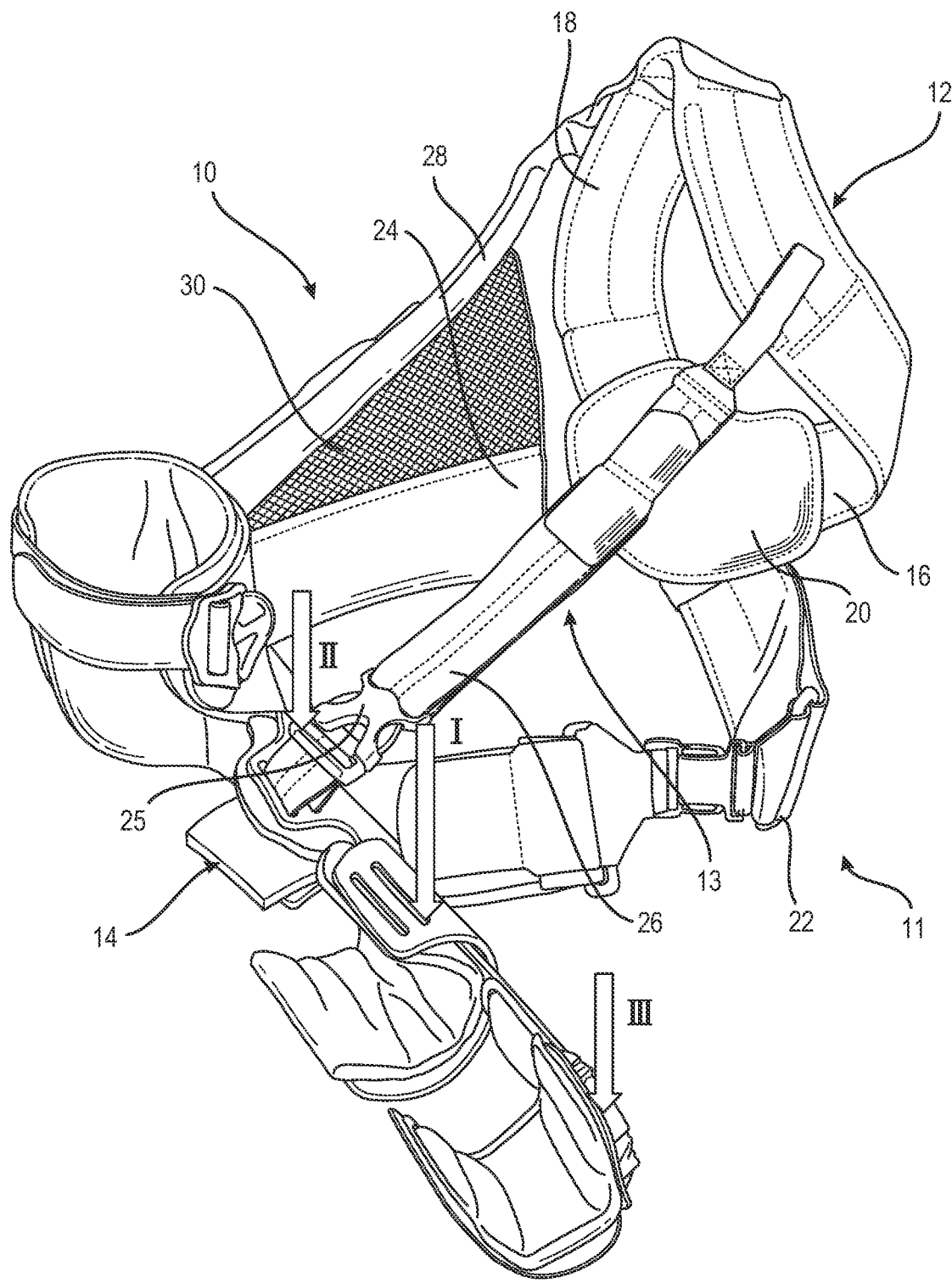
FIG. 1 is a perspective view of an embodiment of a shoulder immobilizer and arm apparatus according to embodiments of the disclosure.

The drawing figures are not necessarily drawn to scale, but instead are drawn to provide a better understanding of the components and are not intended to be limiting in scope but to provide exemplary illustrations. The figures illustrate exemplary configurations of an orthopedic device and in no way limit the structures or configurations of an orthopedic device and components according to the present disclosure.

DETAILED DESCRIPTION OF VARIOUS EMBODIMENTS

A. Introduction

Embodiments of a shoulder immobilizer and arm apparatus may be provided for post-operative use or post-injury range of motion restriction at the shoulder.

Although the embodiments of the disclosure are adapted for supporting and stabilizing anatomical portions of many users having various anatomical shapes and sizes, the embodiments of the disclosure may also be dimensioned to accommodate distinct types, shapes, and sizes of anatomical portions.

A better understanding of different embodiments of the disclosure may be had from the following description read with the accompanying drawings in which like reference characters refer to like elements. While the disclosure is susceptible to various modifications and alternative constructions, certain illustrative embodiments are in the drawings described below. It should be understood, however, there is no intention to limit the disclosure to the embodiments disclosed, but on the contrary, the intention covers all modifications, alternative constructions, combinations, and equivalents falling within the spirit and scope of the disclosure. Unless a term is defined in this disclosure to possess a described meaning, there is no intent to limit the meaning of such term, either expressly or indirectly, beyond its plain or ordinary meaning.

Reference characters are provided in the claims for explanatory purposes only and are not intended to limit the scope of the claims or restrict each claim limitation to the element in the drawings and identified by the reference character.

To ease understanding of the disclosed embodiments of a shoulder immobilizer and arm apparatus, the front or anterior and rear or posterior portions of the shoulder immobilizer and arm apparatus are described independently. The anterior and posterior portions of the shoulder immobilizer and arm apparatus function together to form a shoulder immobilizer that encompasses the user's anatomical portions.

The term "posterior" has its ordinary meaning and refers to a location behind or to the rear of another location. The term "anterior" has its ordinary meaning and refers to a location ahead of or to the front of another location. The posterior and anterior sides are divided by a coronal plane. The term "superior" refers to what is above something, and the term "inferior" to what is below it. The terms "proximal" and "distal" are used to describe parts of a feature close to or distant from the main mass of the body, respectively.

The terms "rigid," "flexible," "compliant," and "resilient" may be used herein to distinguish characteristics of portions of certain features of the shoulder immobilizer and arm apparatus. The term "rigid" should denote that an element is generally devoid of flexibility. Within the context of support members or shells that are "rigid," it should indicate that they do not lose their overall shape when force is applied. The term "flexible" should denote that features are capable of repeated bending; the features may be bent into retained shapes, or the features do not retain a general shape but continuously deform when force is applied. As for the term "semi-rigid," this term is used to connote properties of support members or shells that provide support and are free-standing; however, such support members or shells may have flexibility or resiliency.

The term "compliant" is used to qualify such flexible features as generally conforming to the shape of another object when placed in contact therewith, via any suitable natural or applied forces, such as gravitational forces, or forces applied by external mechanisms, for example, strap mechanisms. The term "resilient" is used to qualify such flexible features as generally returning to an initial general shape without permanent deformation. The term "compressible" may qualify such structural features as being capable of being reduced in size or volume due to the exertion of force applied to the structural feature.

The "affected" or "injured" shoulder is the shoulder at which an injury occurred and is being treated for healing by the embodiments of the disclosure. The "contralateral" shoulder is the shoulder on the side opposite of the affected or injured shoulder.

B. Embodiments of the Shoulder Immobilizer

It is to be understood that not necessarily all objects or advantages may be achieved under embodiments of the disclosure. Those skilled in the art will recognize that the shoulder immobilizer and an arm apparatus may be embodied or carried out, so they achieve or optimize one advantage or group of advantages as taught herein without necessarily achieving other objects or advantages as taught or suggested herein.

The skilled artisan will recognize the interchangeability of various disclosed features. Besides the variations described, other known equivalents for each feature can be mixed and matched by one of skill in this art to construct a shoulder immobilizer and an arm apparatus under principles of the present disclosure. It will be understood by the skilled artisan that the features described may apply to other types of orthopedic, prosthetic, or medical devices.

Although this disclosure describes certain exemplary embodiments and examples of a shoulder immobilizer and an arm apparatus, it nevertheless will be understood by those skilled in the art that the present disclosure extends beyond the specifically disclosed shoulder immobilizer and an arm apparatus embodiments to other alternative embodiments and/or users of the disclosure and obvious modifications and equivalents thereof. It is intended that the scope of the present disclosure should not be limited by the particular disclosed embodiments described above, and may be extended to medical devices and supports, and other applications that may employ the features described.

FIGS. 1-5 exemplify a shoulder brace 10 having a shoulder immobilizer 11 adapted to immobilize a shoulder of a user and to connect to an arm apparatus 14. The shoulder immobilizer 11 and arm apparatus 14 are unique, modular components interchangeable to form the shoulder brace 10. They can be used separately for different treatment protocols, and it is unnecessary that they are combined specifically together. Rather, a clinician can select which component can treat a shoulder and provide corresponding rehabilitation. An abduction pillow, not shown, may be used combined with the shoulder immobilizer 11 and/or arm apparatus 14.

The modular arrangement of the shoulder brace 10 enables this shoulder brace 10 to drop down to a regular shoulder immobilizer instead of being strictly an abduction shoulder brace. The arm apparatus 14 is a rigid open-frame sling and can be modified to attach with a single enclosed loop to function like a regular arm sling. As discussed with FIG. 5, the shoulder immobilizer 11 involves a "double figure-9" strapping arrangement and method arranged to distribute the pressure of supporting an injured arm comfortably by avoiding placement of the shoulder immobilizer 11 neck of the user. The shoulder immobilizer 11 can be modified to function with a soft fabric sling instead of the arm apparatus 14 or combined with another large mechanical device arranged to stabilize and/or propan arm of the user extending from the injured shoulder.

The shoulder immobilizer 11 includes a first portion 12 defining a loop 15 adapted to extend about a contralateral shoulder from the injured shoulder. A second portion 13 of the shoulder immobilizer 11 includes a first belt 22 adapted to extend along an anterior side of a user from a first end of the first portion 12, and a second belt 24 adapted to extend along a posterior side of a user from a second end of the first portion 12. The first and second belts 22, 24 are arranged to couple to one another, preferably on an anterior side A of the user. The second portion 13 is also arranged to secure the arm apparatus 14 when the arm apparatus 14 is utilized.

The first portion 12 comprises first and second segments 16, 18 forming the loop 15. The first and second segments 16, 18 join at an inferior junction 17 adapted at a location generally proximate to the contralateral elbow, such as near the distal terminus of the contralateral humerus. Configuring the inferior junction 17 to be proximate to the contralateral elbow rather than proximate to the contralateral axilla advantageously reduces the angle at which corresponding straps descend from the contralateral shoulder to the arm apparatus 14. This configuration also provides enhanced comfort as heat and chafing underneath the contralateral arm are reduced and minimized pressure points. The first and second segments 16, 18 extend and intersect through a pad 20, generally about the inferior junction 17. The first and second belts 22, 24 extend from the second and first segments 18, 16, respectively, and are arranged at an oblique angle 19 relative to one another. The first and second belts 22, 24 extend from the inferior junction 17 at generally the same height.

Figure 5:
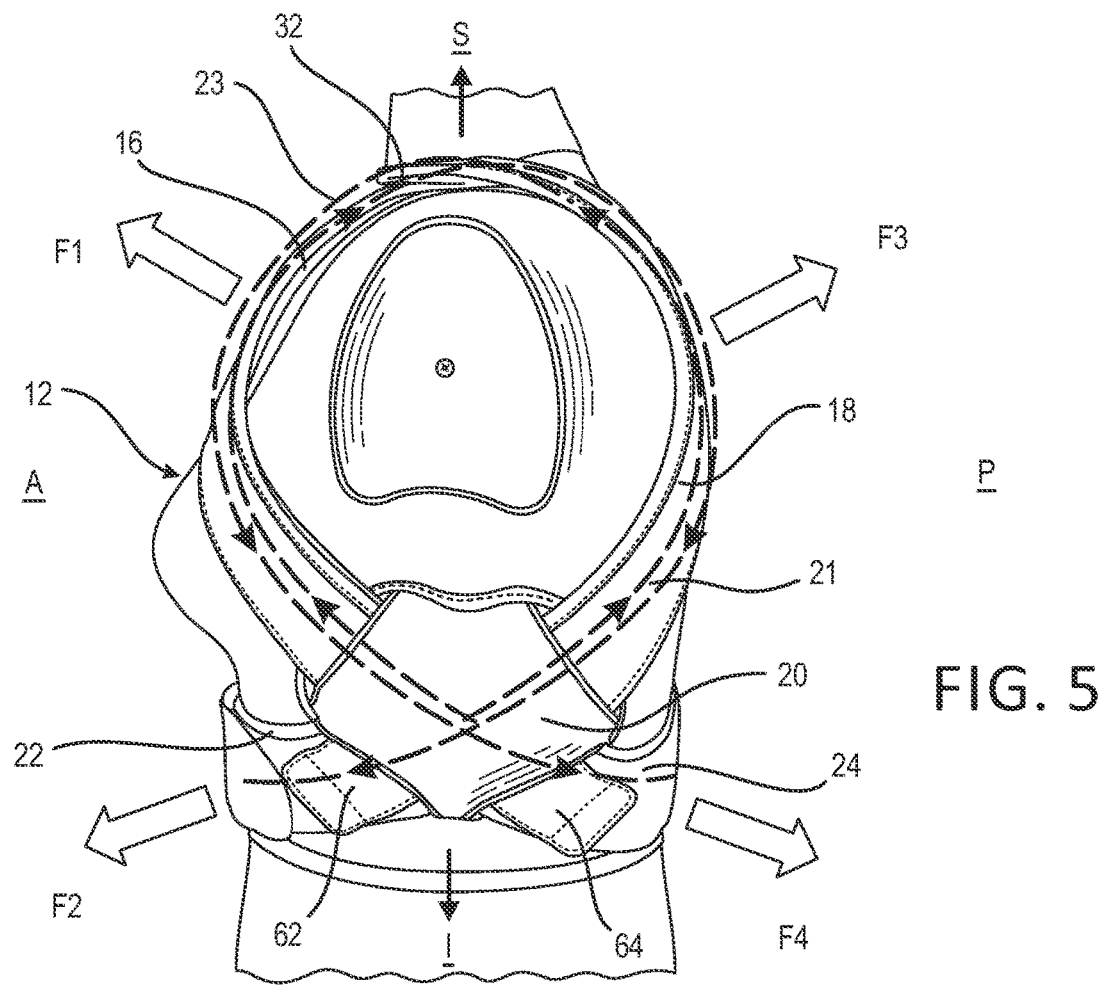
FIG. 5 is a schematic side view of the shoulder immobilizer of FIG. 1 on an uninjured side of a user.

As shown in FIG. 5, the first portion 12 defines the double figure-9 configuration. The first segment 16 is arranged relative to the second belt 24 about the contralateral shoulder when the shoulder immobilizer 11 is tensioned, so a first force F1 superiorly exerted by the first segment 16 counteracts a fourth force F4 inferiorly exerted by the second belt 24 about the contralateral shoulder. The second segment 18 thereof is arranged relative to the first belt 22 about the contralateral shoulder when the shoulder immobilizer 11 is tensioned, so a third force F3 superiorly exerted by the second segment 18 counteracts a second force F2 inferiorly exerted by the first belt 22 about the contralateral shoulder. The first force F1 may extend obliquely opposite to the third force F3, whereas the second force F2 extends obliquely opposite to the fourth force F4.

From the configuration shown in at least FIG. 5, the first portion 12 and the first belt 22 form a first figure-9 strap configuration 21. The first figure-9 strap configuration 21 is arranged to extend in a first direction along the loop 15 inclusive of the first and second segments 16, 18 about the contralateral shoulder, generally extending from the inferior junction 17 to superiorly over the anterior contralateral shoulder. The first figure-9 strap configuration 21 then extends about the posterior contralateral shoulder inferiorly toward the first belt 22 and is arranged to be drawn anteriorly of the user, generally toward force F2. The counteracting strap tension of generated forces F1, F2, F3, F4 is arranged to stabilize the injured arm in internal/external rotation. Strap tension in the first and second segments 16, 18, and/or first and second belts 22, 24 can be intentionally biased to create slight internal/external rotation. In embodiments, the first and second belts 22, 24 are arranged to be equally tensionable, in that they may be coupled to one another by a buckle or coupler.

A second figure-9 strap configuration 23 comprises the first portion 12 and the second belt 24. The second figure-9 strap configuration 23 is arranged to extend in a first direction along the loop 15 inclusive of the first and second segments 16, 18 about the contralateral shoulder, generally extending from the inferior junction 17 to superiorly over the posterior contralateral shoulder. The second figure-9 strap configuration 23 then extends about the anterior contralateral shoulder inferiorly I toward the second belt 24 and is arranged to be drawn posteriorly of the user, generally toward force F4.

The double figure-9 strap configuration evenly distributes the load or loads around the entire uninjured or contralateral shoulder joint, and distributes the loads effectively between a user's hips and an uninjured shoulder. Unlike traditional slings that react the load entirely on the neck or offload neck pressure with a secondary axillary strap that goes underneath the arm but essentially relocates the pressure to the axilla to do so, the double figure-9 is adjusted with equal tension. The four straps including the first and second segments 16, 18, and first and second belts 22, 24 prevent the loop 15 from sliding into the neck and sliding up into the axilla and thereby increasing comfort for a user, particularly over sustained use. Each of the segments 16, 18 and belts 22, 24 counteract one another to create a stabilized arm loop system.

Figure 2:
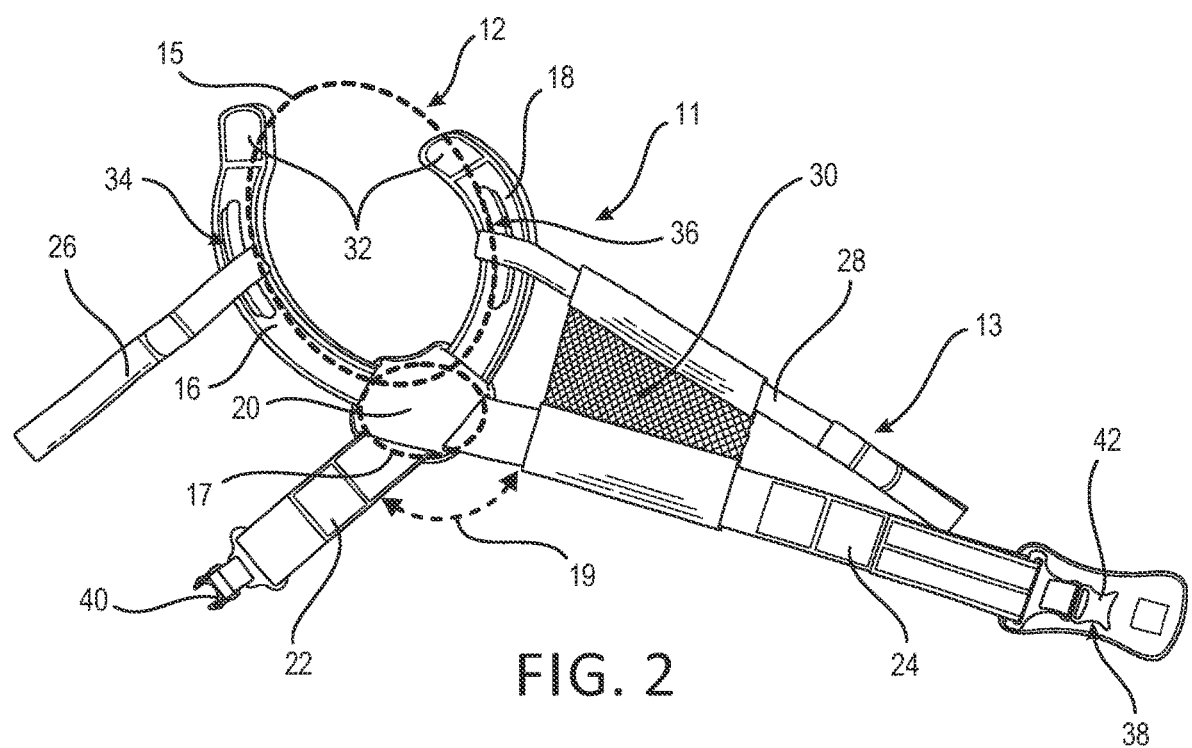
FIG. 2 is a plan view of the shoulder immobilizer of FIG. 1.
Figure 3:
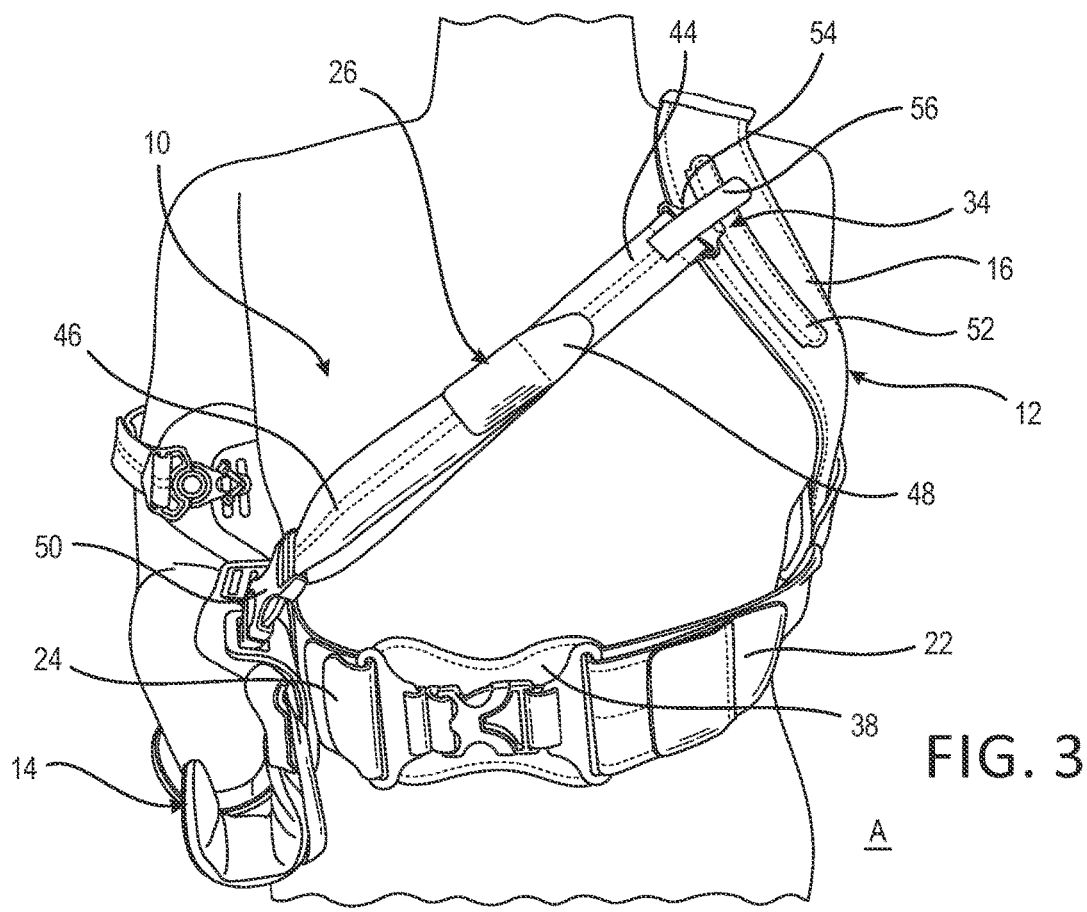
FIG. 3 is a schematic frontal view of the shoulder immobilizer and arm apparatus of FIG. 1 on an anterior side of a user.

Referring to FIGS. 1-3, to further improve stability of the shoulder immobilizer 11 about the uninjured shoulder and correspondingly couple to the arm apparatus 14 or a similar apparatus, the second portion 13 of the shoulder immobilizer 11 may include an anterior strap 26 attachable to the first segment 16 and arranged to secure to the arm apparatus 14. The anterior strap 26 preferably attaches to the first segment 16 at a location superior of the inferior junction 17.

Figure 4:
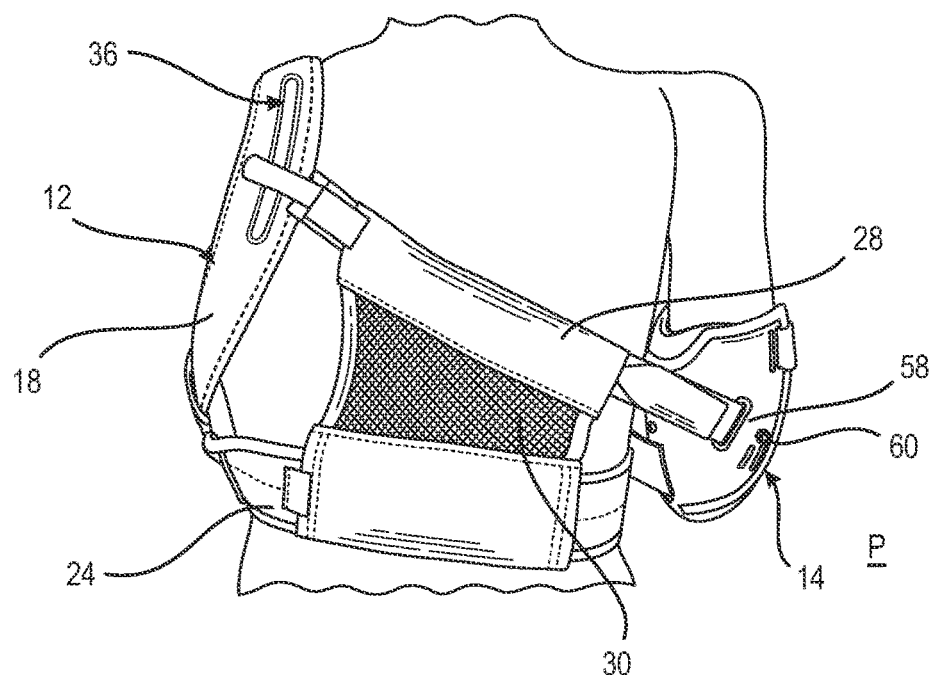
FIG. 4 is a schematic rear view of the shoulder immobilizer and arm apparatus of FIG. 1 on a posterior side of a user.

Referring to FIGS. 2 and 4, the second portion 13 may include a posterior strap 28 attachable to the second segment 18 and arranged to secure the arm apparatus 14. The posterior strap 28 likewise preferably attaches to the second segment 18 at a location superior of the inferior junction 17.

As shown in FIG. 2, the anterior and posterior straps 26, 28 are preferably connected to the loop 15 at the same height. Depending on body type, the height of these connection points may be adjusted to keep the shoulder immobilizer 11 in balance when worn by the user.

Figure 6:
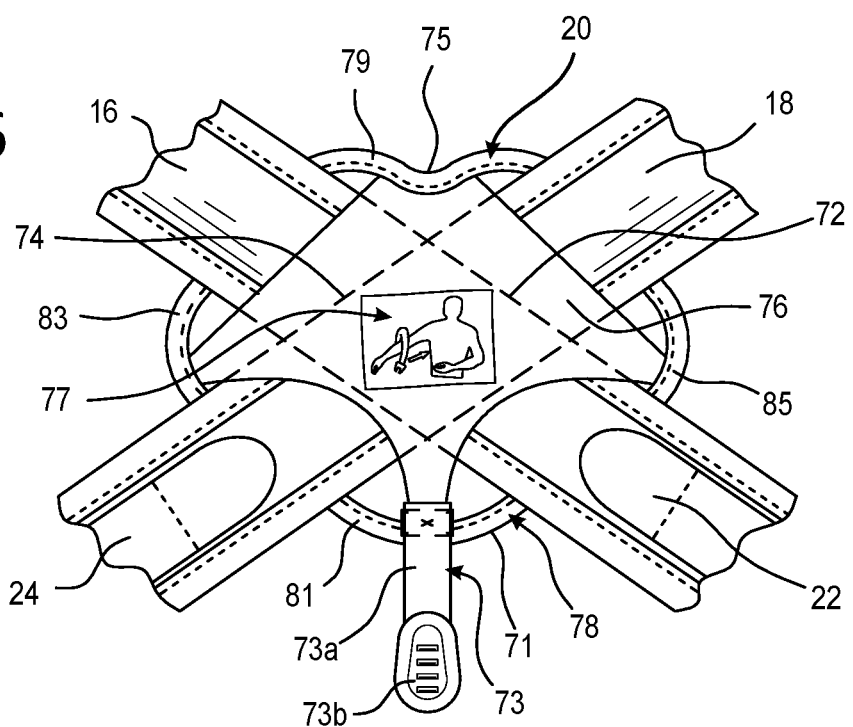
FIG. 6 is a schematic view of a junction pad in the shoulder immobilizer of FIG. 1.

In observing FIG. 2, the anterior and posterior straps 26, 28, and the first and second belts 22, 24 may have intentionally different widths. This indicates to the user to not mix up the straps 22, 24, 26, 28. A wide belt assembly 38 may be more comfortable. Various couplers, buckles, and other attachments are intentionally differently sized or visually distinguishable to prevent a user from attaching the straps to the incorrect locations. For example, visual indicators or indicia and colors can be used as distinguishing visual features. Liners may extend along an inner surface of the first and second portions, or surfaces of the first and second portions may be colored as a visual indication with a color, such as blue, on a side intended to face the body. Artwork images can be placed on the inside of the strapping/liners as visual instructions for correct brace usage, such as along a pad, as shown in FIG. 6. The first and second belts 22, 24 may be provided with first and second buckle components 40, 42, respectively, for securing around the user.

Referring to FIG. 1, the anterior strap 26 can be modified in at least three configurations depending on the user's body type and medical indication. A default configuration may be with the anterior strap 26 attached to a middle attachment point I on the arm apparatus 14. For users that need shoulder subluxation support, the anterior strap 26 can be attached to a proximal attachment point II of the arm apparatus 14 closest to a user's elbow. The proximal attachment point II provides a direct force vector to support the shoulder in the vertical direction. For larger users or those who may want to be fixed in some degree of internal/external rotation, the anterior strap 26 may be attached to the arm apparatus 14 or proximate a distal end at attachment point III. This attachment location relieves the pressure of the anterior strap 26 resting on a user's chest and generates the largest moment arm to resist movement in internal/external rotation. To aid in donning, an end of a buckle 25 connecting the anterior strap 26 to the arm apparatus 14 is preferably arranged in a vertical position, ready to receive the anterior strap 26.

A posterior panel or strap organizer 30 may connect the second belt 24 to the posterior strap 28. The posterior panel 30 may comprise a flexible textile extending between the second belt 24 and the posterior strap 28. The posterior panel 30 may serve as a visual indicator to the user where the brace 10 is front/back and to keep the back straps 24, 28 organized. The flexible textile defining the posterior panel 30 may be breathable and/or elastic to accommodate different sized users and may in embodiments define indicia showing a proper orientation of the shoulder immobilizer 11 for donning and doffing purposes.

Figure 7:
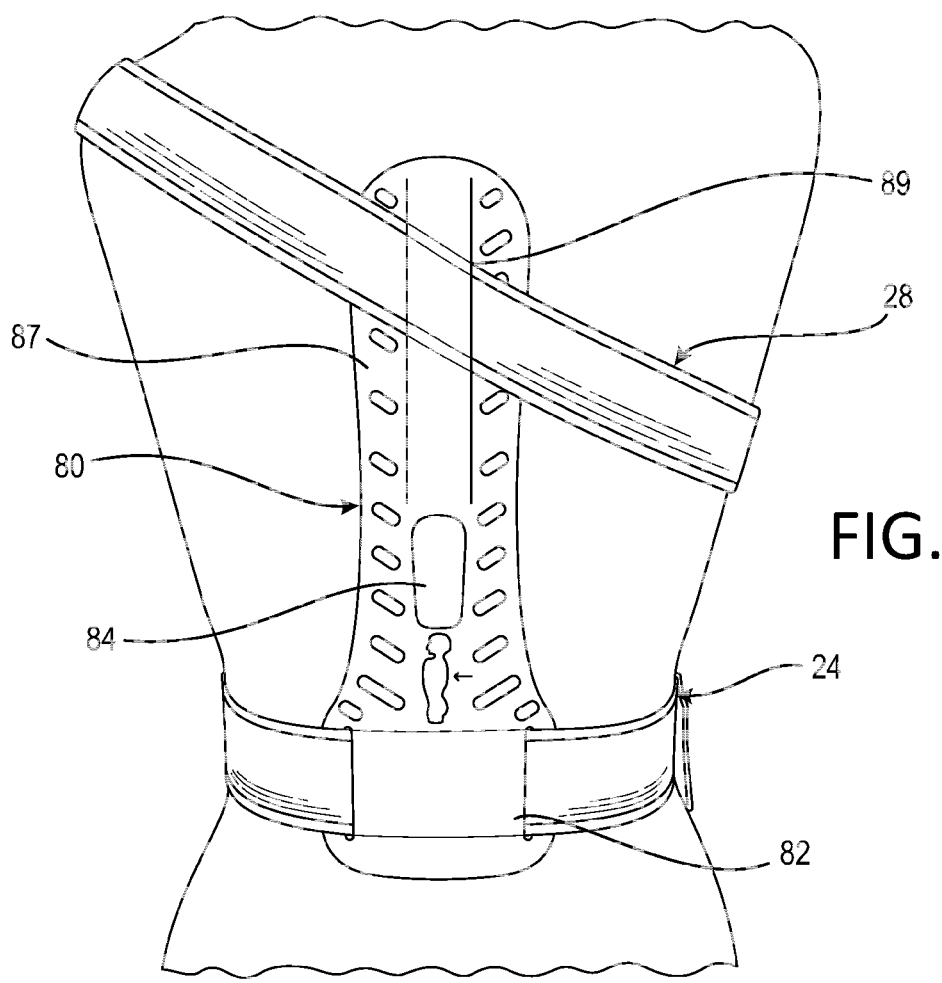
FIG. 7 is a schematic rear view of a variation of the shoulder immobilizer of FIG. 1 on a posterior side of a user.

As shown in FIG. 7, the posterior panel 30 may be a plate 80 having rigid or semi-rigid properties and arranged as a strap organizer. The plate 80 may define a plurality of openings 84. The second belt 24 slidably extends through the plate 80 through at least one retainer or slot 82. The posterior strap 28 slidably extends through the plate 80 through at least one retainer or slot 89. The plate 80 preferably has a profile or shape 87 adapted to extend along the user's spine comfortably. Additionally, the plate 80 may be arranged to provide comfortable support for the user by providing resiliency and rigidity sufficient to resist excessive movement in either forward or backward movements.

As the back strapping can be perceived as confusing/intimidating when seen by unfamiliar eyes, the strap organizer 30, 80 can be placed on the posterior side of the shoulder immobilizer 11 to give the user an obvious visual cue as to how the shoulder brace 10 should be oriented to reduce the visual complexity of the overall assembly. While described with certain features, the strap organizer 30, 80 has no strict requirements. For example, it may include a mesh fabric, regular woven fabric, EVA foam, or injection molded plastic. The strap organizer 30, 80 is arranged for the posterior strap 28 and/or second belt 24 to pass through freely. The strap organizer 30, 80 may resist a tendency for the posterior strap 28 and second belt 24 to twist and wrap around each other when the shoulder brace 10 is not being worn, making the shoulder brace 10 easier to store at a clinician's office. As the strap organizer 30, 80 floats relative to the posterior strap 28 and second belt 24, a clinician may remove it in its entirety.

Returning to FIG. 2, the first and second segments 16, 18 may have their superior end portions detachably secured at a superior location by at least one attachment 32. The center of the loop 15 separates at an attachment area, for example, the at least one attachment 32 being from an attachment material such hook & loop material, to open the loop 15. This opening feature of the loop 15 is arranged to allow a clinician to fit the loop 15 over an unconscious user's uninjured arm when IV tubes, blood-pressure cuffs, or other medical equipment may be attached.

The ability to open the loop 15 at the superior S location allows for an additional extension piece (not shown) to be added to the first and second segments 16, 18 if the user has a shoulder diameter beyond that provided by the first and second segments 16, 18. The opening is intended to be discrete and infrequently opened by the practitioner, such as for the initial fitting on the user. In embodiments, the at least one attachment 32 is not intended to be modified by the user. The at least one attachment 32 is preferably arranged so one end of one of the first and second segments 16, 18 overlaps the other to eliminate any chance of exposed attachment material irritating the skin of the user if improperly placed.

FIGS. 2, 5 and 6 exemplify the first and second segments 16, 18 extending and intersecting through the pad 20 generally located about the inferior junction 17, and the first and second belts 22, 24 extending from the second and first segments 18, 16, respectively, at an oblique angle 19 relative to one another. First and second coupling parts 62, 64 removably secure the first segment 16 to the second belt 24 and the second segment 18 to the first belt 22, preferably outside of the inferior junction 17 and the pad 20. The first and second coupling parts 62, 64 may be secured to the pad 20 and generally extend parallel to the first and second belts 22, 24. The first and second coupling parts 62, 64 may likewise attach to the first and second segments 16, 18.

Coupling by the coupling parts 62, 64 may be achieved through a variety of fastener means, such as hook and loop whereby surfaces of the first and second segments 16, 18 and/or the first and second belts 22, 24 may have hook-receivable material. The provision of the first and second coupling parts 62, 64 advantageously allows for a position of the first and second segments 16, 18 relative to the first and second belts 22, 24 to be secured by the user or a clinician, and thereby setting the desired level of tension in the shoulder immobilizer 11. The first and second coupling parts 62, 64 further enhance the comfort and compliant use of the shoulder immobilizer 11 by facilitating customization of the shoulder immobilizer 11 to a user's dimensions and activities.

FIG. 6 schematically shows the pad 20 arranged with first and second channels 72, 74 separate from one another and accommodating the second and first segments 18, 16, respectively. Inferior end portions of the first and second segments 16, 18 are slidable within the second and first channels 74, 72. The pad 20 preferably has a covering 76 extending over the first and second channels 72, 74. The first and second channels 72, 74 are arranged to maintain the first and second segments 16, 18 in a fixed spatial relationship at the inferior junction 17, whereas during adjustment of the first and second segments 16, 18 slide relative to one another. Once the first and second coupling parts 62, 64 shown in FIG. 5 secure to the first and second belts 22, 24, sliding of the first and second segments 16, 18 is mitigated.

The covering 76 preferably includes indicia 77 for prompting a user regarding the orientation to install the first portion 12. The indicia 77 is preferably located on an underside or interior side I of the covering 76 and intended to be adjacent to the user when donned. The pad 20 has a profile 78 defining a recess 79 at a superior side 75, a peak 71 at an inferior side 81, and widened sides 83, 85 toward the superior side 75. The profile 78 is arranged to ergonomically accommodate the inferior shoulder and armpit and the user's torso by evenly distributing pressure on the contralateral side of the user through at least the widened sides 83, 85 extending inferiorly of the shoulder. The size of the pad 20 may be selected according to a side of a user to improve pressure distribution about the user's torso.

A pull tab 73 may be provided at the peak to help a user properly position the contralateral shoulder comfort loop during donning. The pull tab 73 includes a strap 73a and may have a tab 73b extending from the strap 73a. The tab 73b may be constructed from plastic and have traction elements, whereas the strap 73a may include a flexible textile. The tab 73b is preferably harder than the strap 73a.

FIGS. 1-3 and 8 exemplify height adjusters that may be provided on the first and second segments 16, 18 for adjusting the anterior and posterior straps 26, 28 connected to and extending therefrom. For example, the anterior strap 26 may be slidably attached to the first segment 16 by a first height adjuster 34. The posterior strap 28 is slidably attached to the second segment 18 by a second height adjuster 36. Both the first and second height adjusters 34, 36 may be similarly arranged.

The height adjusters 34, 36 are arranged to be directly secured to the first and second segments 16, 18. This arrangement allows a clinician to adjust a vertical position of the anterior or posterior straps 26, 28 attach to the loop 15 without physically removing the straps 26, 28. This arrangement removes a need to remove one of the anterior and/or posterior straps 26, 28 from the loop 15, causing confusion and resulting in misapplication or sizing issues. The height adjusters 34, 36 may have a plurality of predetermined landing locations. The height adjusters 34, 36 may adjust the height of an end portion of the anterior and posterior straps 26, 28 relative to the loop 15.

Using the first height adjuster 34 for example, the first height adjuster 34 includes a slider 52 connected to the first segment 16 and a coupler 54 slidably engaging the slider 52. The coupler 54 engages the anterior strap 26. A flap 56 may extend from the anterior strap 26 and engage a surface of the first segment 16 to add extra security to the engagement of the anterior strap 26 to the first segment 16. The flap 56 may comprise any suitable material and may allow the coupler 54 to be releasably retained at a particular height or location along with the slider 52. This provides a user and/or clinician with an infinitely large number of possible configurations of the strap 26, facilitating a uniquely customizable shoulder immobilizer 11.

In a preferred embodiment, the first height adjuster 34 includes a coupler 54 having a spring assembly 86 adjustably engaging the slider 52 among a plurality of predetermined locations 91*a*, 91*b*, 91*c* spaced apart from one another by at least at one predetermined distance. The slider 52 has an elongate member 88 defining a rib 90 proximate an edge 93 thereof along which the spring assembly 86 slides. The spring assembly 86 is preferably biased against the edge 93. The elongate member 88 may have an arcuate shape 87 generally conforming to a contour of the first segment 16. The rib 90 protrudes from the elongate member 88 and defines a plurality of notches or detents 91*a*, 91*b*, 91*c* located on an inner side of the rib 90 opposite the edge 93.

Figure 8A:
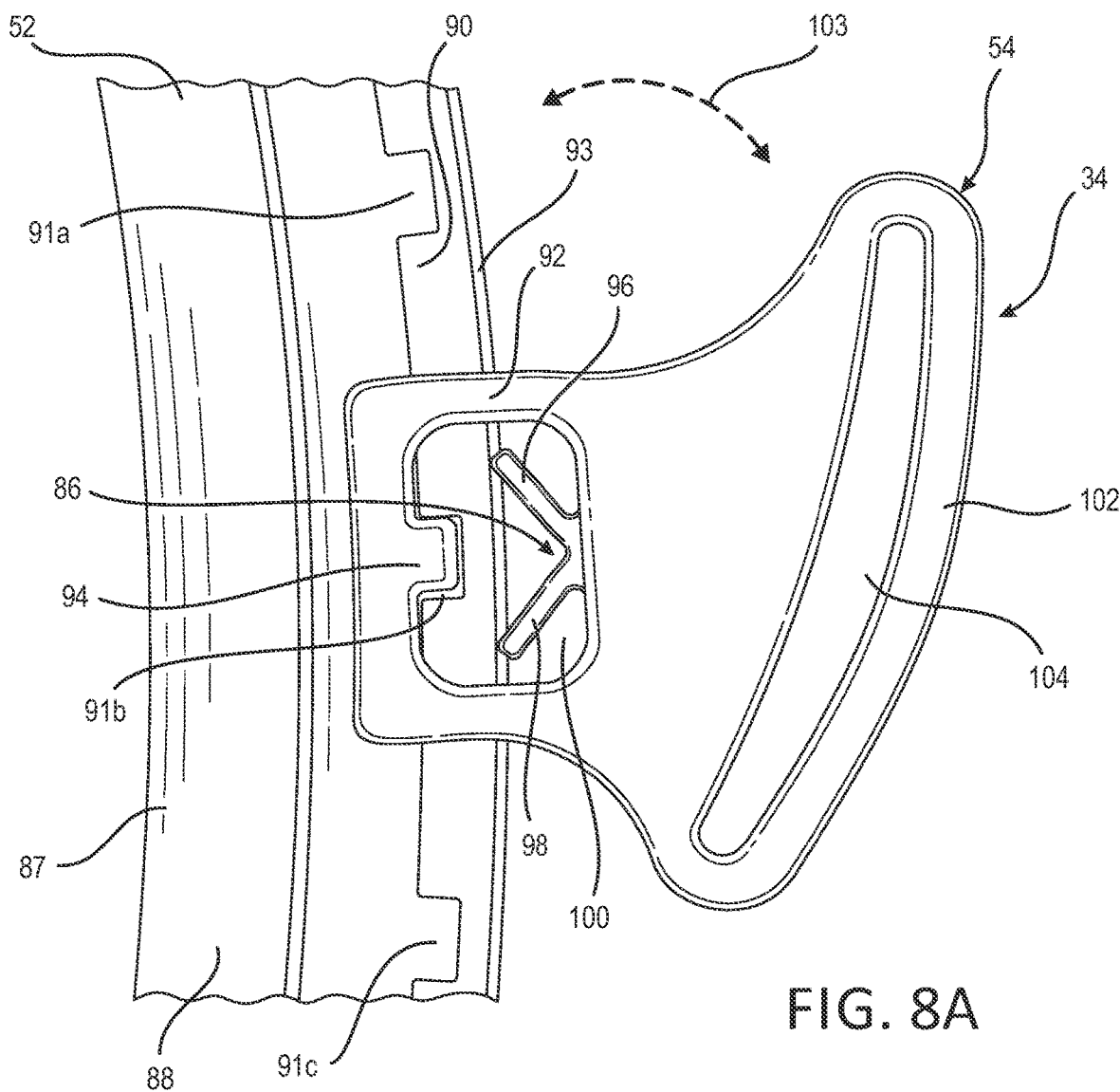
FIG. 8A is a schematic view of a height adjuster assembly in the shoulder immobilizer of FIG. 1.
Figure 8B:
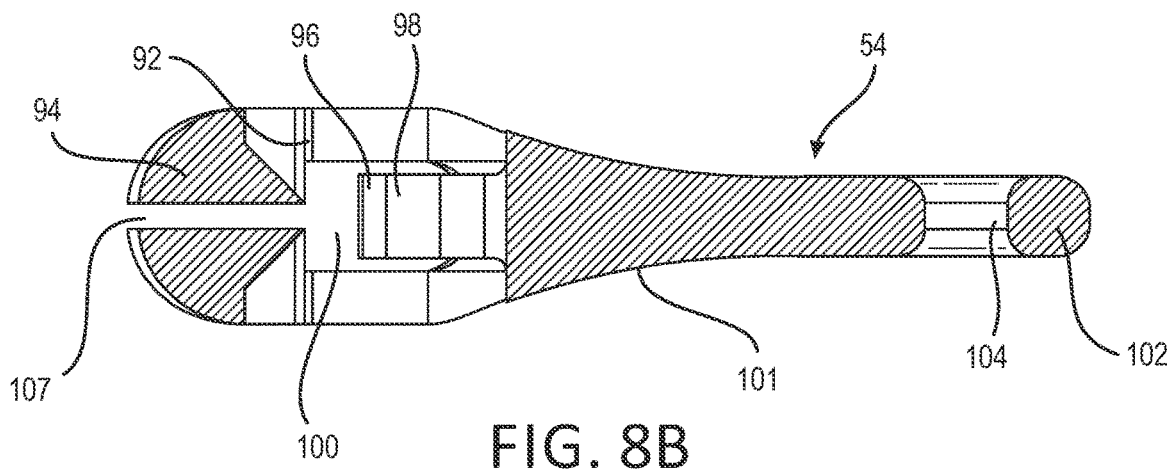
FIG. 8B is an elevational view of the height adjuster assembly of FIG. 8A.

The coupler 54 forms a window 100 surrounded by a frame 92 protruding from a side of the coupler 54 opposite a retainer 102, forming a slot 104 for receiving the anterior strap 26. The coupler 54 forms a tab 94*a* extending inwardly into the window 100 along an inner side and arranged to engage one notch 91*a*, 91*b*, 91*c* to prevent sliding along the slider 52. Tabs 94*a* may be defined on both top and bottom sides of the frame 92. The tabs 94*a* may define a clearance 107 between them configured to abut the slider 52 therethrough, facilitating sliding translation of the coupler 54. As seen in FIG. 8B, the coupler 54 may define a profile 101 from a first thickness at the frame 92 sloping to the thinner thickness at the retainer 102.

The rib 90 may define a terminus 105 proximate an end region 106 of the slider 52. The terminus 105 may be sized and configured to arrest translation of the coupler 54 near the end region 106 by, for example, defining a flat surface against which a surface of the frame 92 may abut near the terminus 105.

The coupler 54 defines or comprises at least one spring element 96, 98, such as a leaf spring, extending into the window 100 oppositely from the tab 94*a*. The at least one spring element 96, 98 is adapted to bias against the edge 93 and relax when one notch 91*a* receives the tab 94*a*, 91*b*, 91*c*. In operation, urging of the coupler 54 towards edge 93 deflects the at least one spring element 96, 98 to push the tab 94*a* out from the notch 91*a*, 91*b*, 91*c*.

As the coupler 54 slides along the rib 90 between notches 91*a*, 91*b*, 91*c*, the at least one spring element 96, 98 deflects and relaxes from deflection to lock the tab 94*a* into one notch 91*a*, 91*b*, 91*c* once properly positioned. A user or clinician is thereby enabled to provide a robust and reliable attachment between the anterior strap 26 and the first segment 16 while also facilitating intuitive and convenient adjustment of the anterior strap 26.

The at least one spring element 96, 98 may be a bar arranged at an angle relative to the rib 90. The retainer 102 is preferably arranged at an acute angle 103 relative to the rib 90. The retainer 102 and the rib 90 preferably each have an arcuate profile to accommodate the shape of the loop 15, although the height adjuster 34 may be straight or have another form of a profile according to the intended use while permitting sliding of the coupler relative to a rib. Sheet material or fabric of the first segment 16 preferably covers the member 88 aside from the rib 90, which protrudes from the first segment 16 and has sufficient clearance for the coupler 54 to engage therewith freely and permit adjustability relative thereto.

Figure 8C:
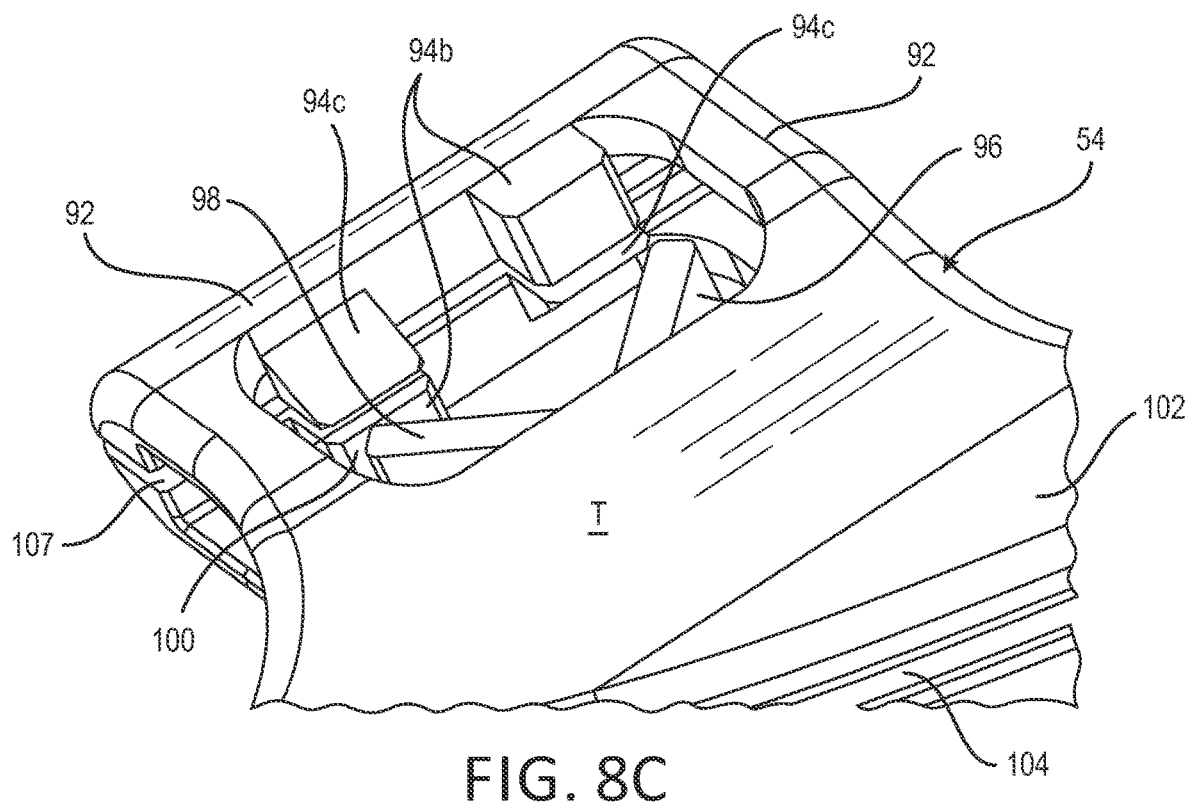
FIG. 8C is a perspective view of the height adjuster assembly of FIG. 8A.
Figure 8D:
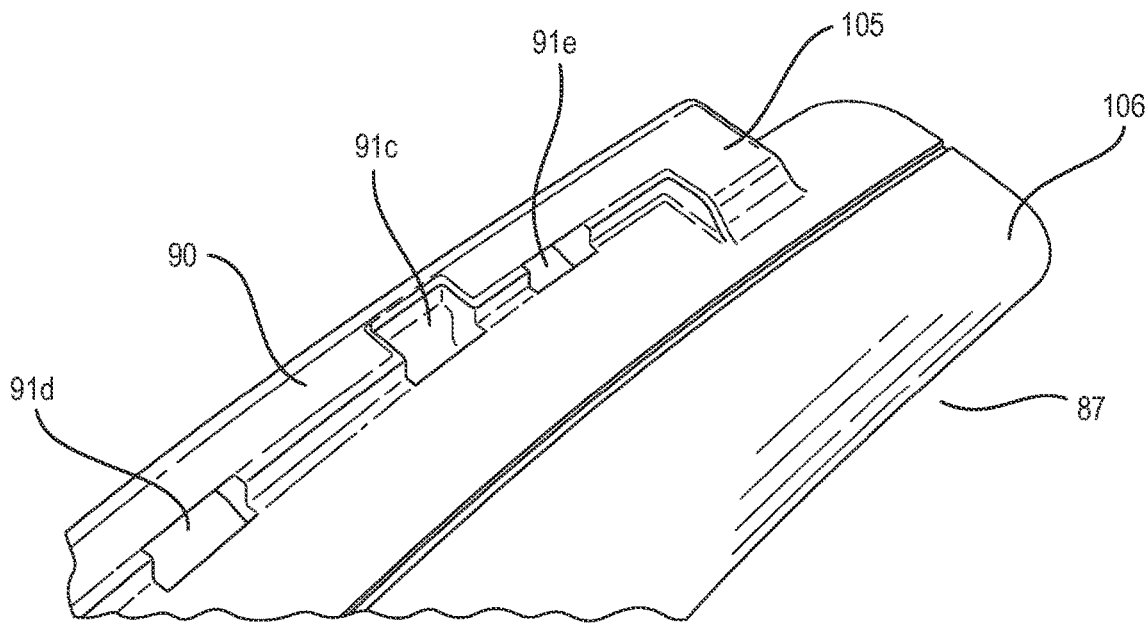
FIG. 8D is a perspective view of the height adjuster assembly of FIG. 8A.
Figure 8F:
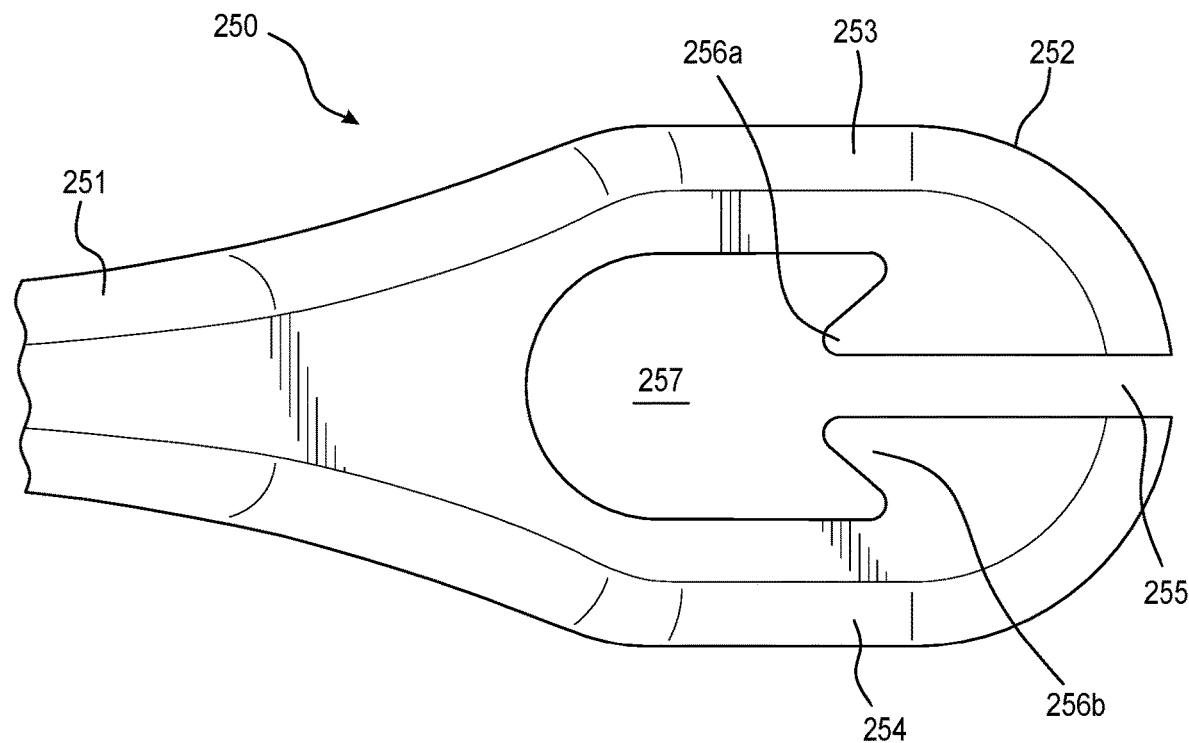
FIG. 8F is a sectional and elevational view of a variation of the height adjuster assembly of FIG. 8A.
Figure 8G:
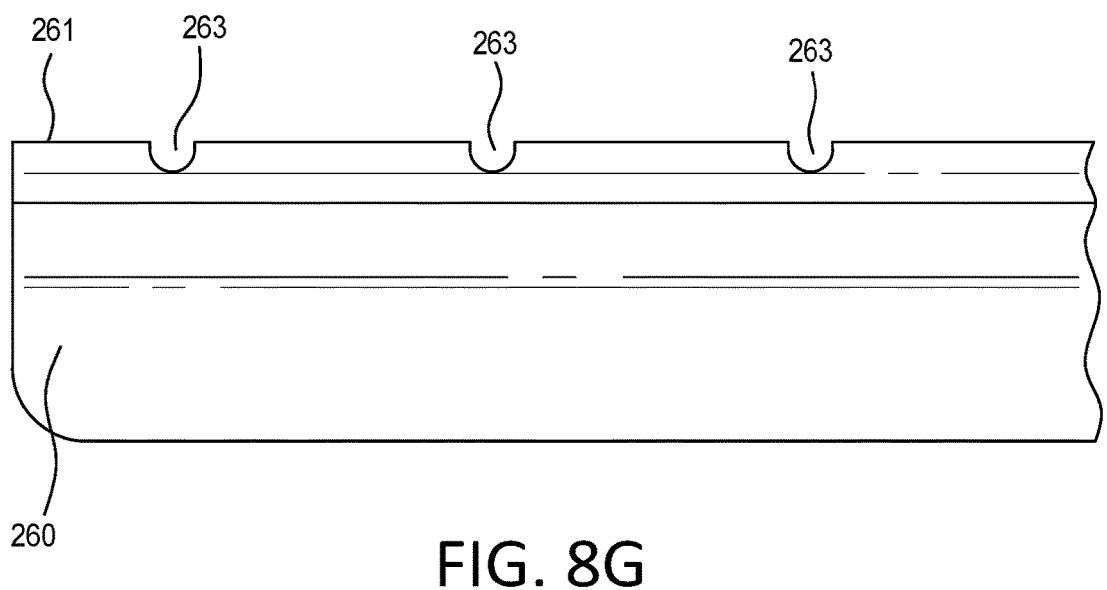
FIG. 8G is sectional view of a variation of a slider of the height adjuster assembly of FIG. 8A.
Figure 8E:
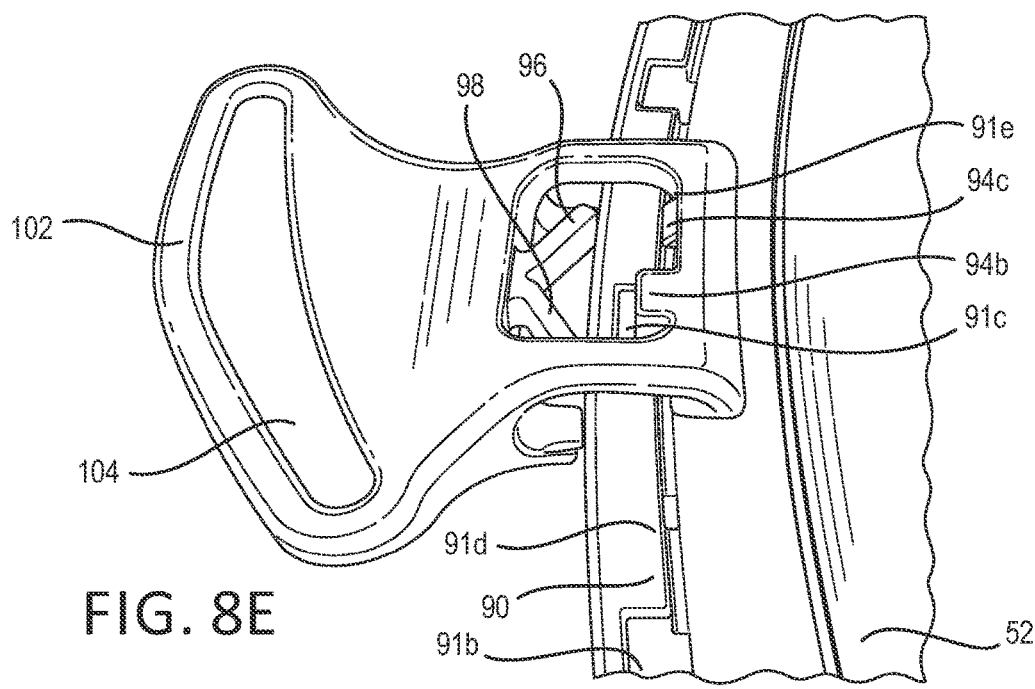
FIG. 8E is a perspective view of the height adjuster assembly of FIG. 8A.

In another embodiment depicted in FIGS. 8C-8E, the coupler 54 may advantageously define differently shaped tabs 94*b*, 94*c* that are arranged to cooperate with corresponding recesses or detents 91*c*, 91*e*. The tabs 94*c* may be ramp-shaped in correspondence with ramp-shaped detents 91*e*, which can be configured to receive the tabs 94*c*. By contrast, the tabs 94*b* may, like the tabs 94*a* shown in FIGS. 8A and 8B, be square or rectilinear in shape. As seen in FIGS. 8C-8E, the tabs 94*b*, 94*c* can be defined on both sides of the coupler 54 and may alternate in position. For instance, on a first or top side T shown in FIG. 8C, the tab 94*c* is arranged adjacent to or near a tab 94*b*, having a square shape. On the opposing side, another tab 94*c* is arranged with a back side thereof adjacent or near a back side of the tab 94*b* from the top side T. Likewise, another tab 94*b* is arranged adjacent or near the second tab 94*c* with a back side thereof arranged adjacent or near a back side of the tab 94*c* from the top side T.

The corresponding recesses 91*c*, 91*e* may have shapes corresponding to the ramp-shaped and tabs 94*c*, 94*b*; that is, the recesses may be ramp-shaped and square-shaped to receive and engage with the ramp and square shapes of the tabs 94*c*, 94*b*. In use, both the tab 94*c* and the tab 94*b* may engage with the corresponding ramp-shaped and square-shaped recesses 91*e*, 91*c* to prevent unintentional sliding or failure of the shoulder immobilizer 11, preventing injury or disruption to a user's recovery.

A challenge of parts that slide along an open channel is the sliding part's tendency to open when pulled in tension. To prevent failure of the coupler 54 when pulled in tension during immobilization and support of a shoulder and arm, such as by the clearance 107 being widened under tension to the point of disengagement of the coupler 54 and the slider 52, the corresponding tabs 94*c*, having a ramp-shape, and recesses 91*e* are provided.

The engagement between the tabs 94*c* and the ramp-shaped recesses 91*e* in particular prevent the clearance 107 from being widened under tension to the point of disengagement between the coupler 54 and the slider 52, as the frame 92 is prevented from extending outward relative to the slider 52 due to the engagement between the tabs 94*c* and the recesses 91*e*. The depicted embodiment thus advantageously controls translation of the coupler 54 along with the slider 52 and prevents deformation of the coupler 54, ensuring that use of the height adjuster 34 is intuitive, reliable, and safe.

FIG. 8F is another embodiment of a coupler 250 for the height adjustment assembly and useable with the slider 260. The coupler 250, while shown in a sectional view, is intended to have a retainer as in FIG. 8A. The couple 250 has an undercut 256*a*, 256*b* along both sides 253, 254 over the entire length to increase engagement and reduce risk of opening at the clearance 255 at the head 252. The undercuts 256*a*, 256*b* combined with the head having a clearance 255 allows the coupler 250 to engage the slider 260. The removal of the at least one spring element, in comparison to FIG. 8B, provides for a more flexible coupler.

FIG. 8G exemplifies a slider 260 as being straight to accommodate the undercut 256*a*, 256*b* of the coupler 250. The slider has a surface 261 along which the coupler slides and engage notches 263.

It will be appreciated that the depicted arrangement is merely exemplary and that the spring may take any suitable form or be formed of any suitable material. In embodiments, the at least one spring element is press-fitted into the coupler 54, while in other embodiments the at least one spring element is integral therewith. The tabs and recesses may further be provided in any suitable shape, material, and number.

FIGS. 2 and 3 illustrate the anterior strap 26 having a first strap portion 44 connecting to the first segment 16 by the first height adjuster 34 and the arm apparatus 14 by a connector 50. The anterior strap 26 has a second strap portion 46 extending from the connector 50 and detachably securing to the first strap portion 44 to adjust the length of the anterior strap 26.

FIG. 4 shows an end portion of the posterior strap 28 coupling to a posterior portion of the arm apparatus 14 by a mount 60. The end portion of the posterior strap 28 rotatably coupled to the mount 60 by a retainer 58. The mount 60, as seen, may be shaped to facilitate rotational coupling, for example, by defining in embodiments a ball-and-socket type joint. The posterior strap 28 is preferably adjustable in length at the retainer 58.

Figure 9A:
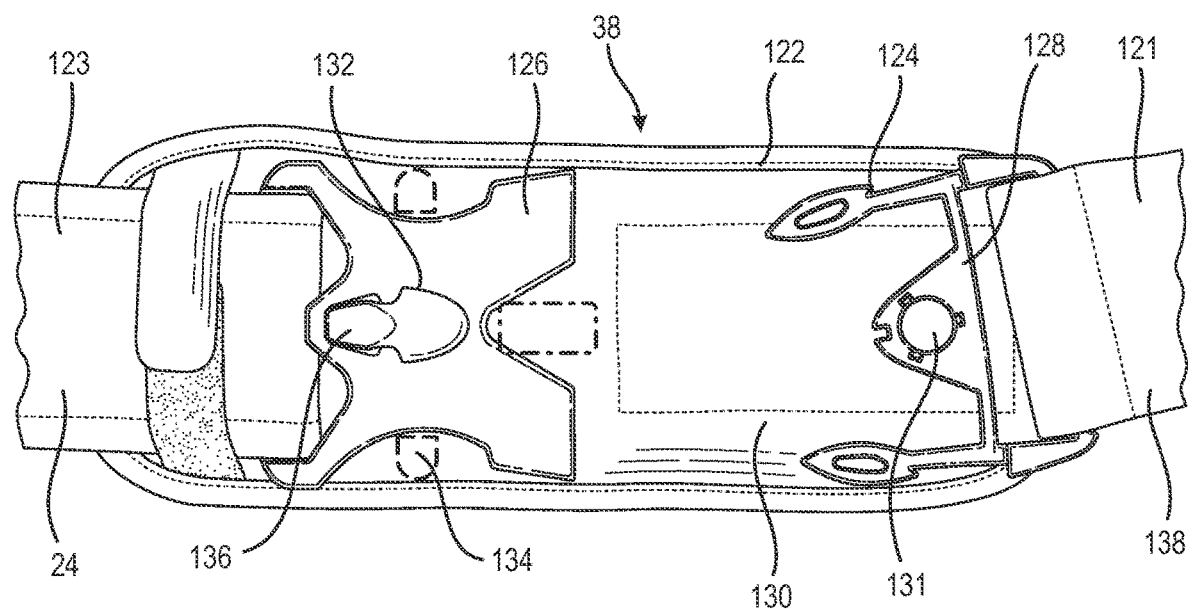
FIG. 9A is a schematic view of a belt assembly in the shoulder immobilizer of FIG. 1.

FIG. 9A illustrates the first and second belts 22, 24 securing to one another by a belt assembly 38. During user donning, a belt assembly may be difficult to attach with a single hand, particularly when the arm of an injured shoulder is immobilized in an arm apparatus. The belt assembly 38 is arranged by recognizing this need and is arranged for single-hand attachment of the first and second belts 22, 24. Generally, one end of the belt assembly 38 is in a fixed location on a mounting pad 122, such as an end portion 123 of the second belt 24, to make it easy for a user to attach an end portion 121 of the first belt 22 without additional support or manipulation. Both end portions 121, 123 of the first and second belts 22, 24 are preferably fed through a buckle assembly having buckle parts 124, 126 for size adjustability.

The buckle part 126 that may be fixed to the mounting pad 122 or the end portion 123 of the second belt 24 may be fixed to the mounting pad 122 at location 134, enabling the buckle part 126 to pivot relative to the mounting pad 122. The attachment of the buckle part 126 and/or end portion 123 of the second belt 24 to the mounting pad 122 provides a user with a large feature to grab to control the buckle part more easily 126 with a single hand. The mounting pad 122 functions to relieve pressure from the buckle parts 124, 126 when the belt assembly 38 is tightened.

The buckle parts 124, 126 are arranged with ergonomic features. One buckle part 124 has an enlarged opening 128 that the user can hook a thumb into, and the other end has a two-finger indentation that a user can place their fingers onto to use an ergonomic pinching motion to close the buckle 124, 126 with one hand.

The mounting pad 122 may include a first attracting element or magnet 131 associated therewith. The second buckle part 126 has a second attracting element or magnet 130 arranged to cooperate with the first attracting element or magnet 131 of the mounting pad 122. The first attracting element or magnet 131 is preferably located proximate or at the first buckle part 124.

Regarding the magnet connection between the first and second attracting element magnets, a small sheet steel landing area may be sewn into the construction of the mounting pad 122. When the buckle part 124 is brought near the mounting pad 122, the magnet 131 will pull the belt end onto the mounting pad 122, placing it in a position adjacent to the other buckle part 126 ready to receive it. This promotes easy and ergonomic buckle closure without having to struggle to align the belt ends 121, 123. The required strength of the magnet 130, 131 can be determined according to the desired attraction onto the mounting pad 122. Magnetic force provides a feeling of security and an indication to the user of proper use/placement of the buckle. When the buckle part 124 is released the magnet 130, 131 will want to retract the buckle part 124 in a controlled manner so the end portion 121 does not fall away.

Figure 9B:
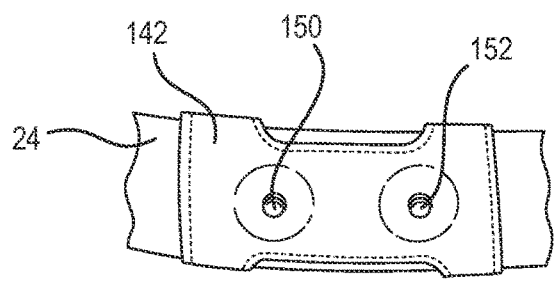
FIG. 9B is a schematic view of a sheath on the belt assembly for securing an arm apparatus.

FIG. 9B exemplifies a sheath 142 that may be slidably or fixedly mounted on the belt assembly 38, such as the second belt 24 for coupling the belt assembly 38 to the arm apparatus 14. The sheath may have at least one fastener 150, 152 adapted to engage a corresponding fastener of the arm apparatus 14. For example, at least one fastener 150, 152 may be a snap fastener, as depicted, or hook and loop. With a snap fastener, it may be sewn into the sheath 142, and the sheath 142 may slide along the second belt 24 to position the sheath 142 relative to how the arm apparatus 14 extends on a unique user relative to the belt assembly 38. In alternative embodiments, the sheath 142 is omitted and at least one fastener 150, 152 may be implanted in a particular part of the strap 24 for attachment to the arm apparatus 14.

Figure 10A:
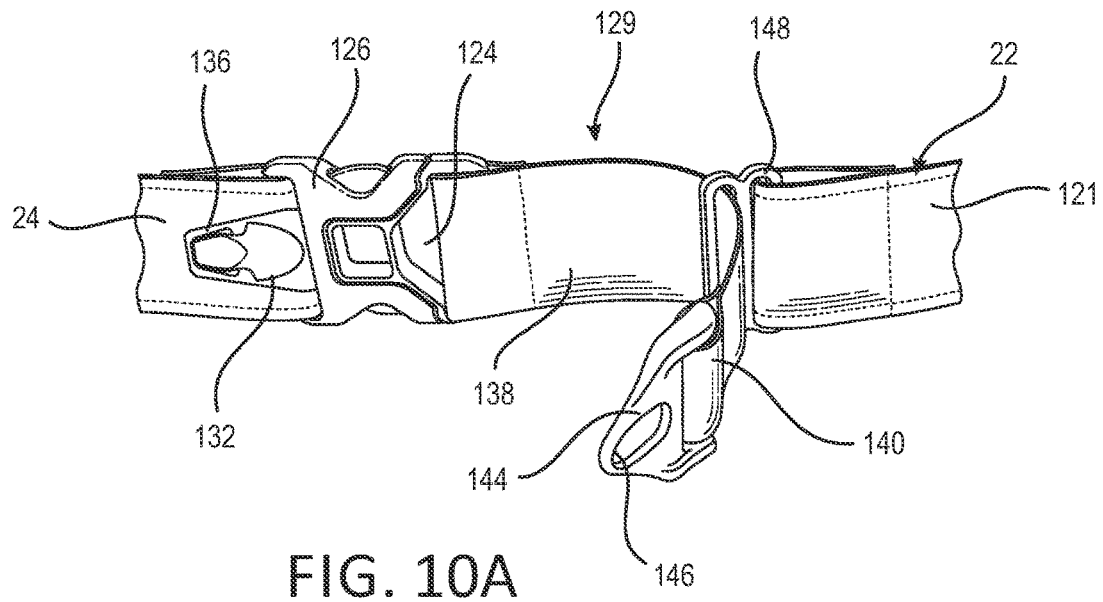
FIG. 10A is a schematic view of the belt assembly of FIG. 9A.
Figure 10B:
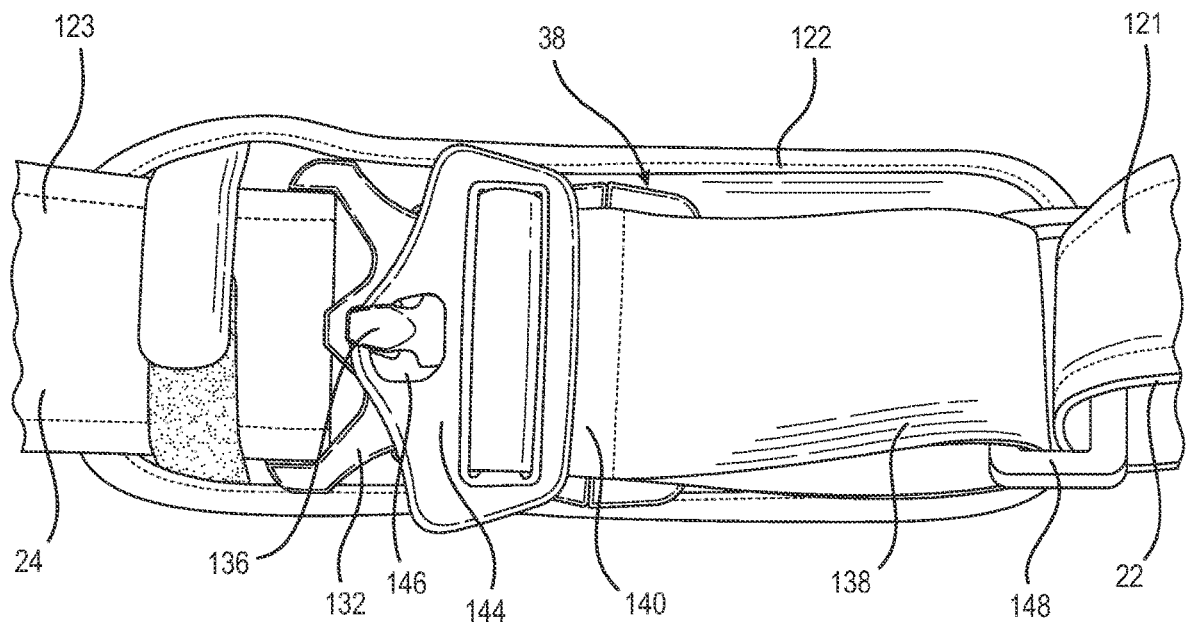
FIG. 10B is a schematic view of the belt assembly of FIG. 9A.

FIG. 10A shows a variation of an easy-fit buckle used to cinch the belt assembly 38 to a properly adjusted length. The easy-fit buckle includes a strap retainer 132 at the first end portion of the buckle part 126. The strap retainer 132 has a hook element 136 arranged for coupling to a retainer 140 bearing a strap connector 138 and having a connecting portion 144 defining an opening 146 corresponding to the hook element 136. The strap connector 138 couples to the end portion 121 of the first belt 22 by a ring 148. The first strap connector 138 is adjustable in length about the ring 148 and coupled to the hook element 136. The hook element 136 may be formed or attached to the buckle part 126. The user is forced to undo both buckles to doff the brace by attaching the easy-fit buckle to the buckle part. If the user does not cinch the strap, the brace will not be as stable but does provide relief when sitting or after meals.

The easy-fit buckle further facilitates easier and more intuitive donning by a user or a clinician, as the added slack that results when the hook element 136 and opening 146 are disengaged makes the shoulder brace 10 easier to place on the user's body properly. As seen, the ring 148 defines an aperture sized to allow sliding engagement of the strap connector 138 without allowing passage of the retainer 140. The arrangement of the strap connector 138 thus allows for the circumference of the shoulder immobilizer 11, and therefore slack in the shoulder immobilizer 11, to be temporarily increased during donning or doffing by disengaging the hook element 136 and the opening 146, which allows the strap connector 138 to slidingly translate through the aperture of the ring 148, which increases an overall circumference of the shoulder immobilizer 11. The arrangement of the strap connector 138 retains the ability to be re-tightened to a consistent circumference when the opening 146 and the hook element 136 are re-engaged, for example, after donning.

In embodiments, the second belt 24 may be provided with a plurality of attachment points, which may be formed as hooks 136, along a length of the second belt 24, thereby providing a plurality of circumferences, tensions, and/or amounts of slack for customization to the particular dimensions of each user.

The provision of the strap connector 138 further provides additional security for a user. If the buckle parts 124, 126 fail, and disconnect from each other, the strap connector 138, including the corresponding hook element 136 and opening 146, retain the shoulder immobilizer 11 in a substantially entirely closed configuration, preventing the immobilized shoulder from moving to a detrimental degree.

It will be understood that the above embodiments are merely exemplary, and a shoulder immobilizer according to the disclosure may have any suitable configuration or components. The straps may comprise any suitable material and may be provided in any suitable configuration. The shoulder immobilizer may be formed as a soft good, with conventional bracing components, or in any other suitable manner.

The embodiments of a shoulder immobilizer described above advantageously solve the problem of existing shoulder immobilizers being uncomfortable to wear and difficult to don and doff. According to the disclosure, the shoulder immobilizer embodiments overcome the problem of existing shoulder-immobilization solutions creeping or extending into the neck and axilla regions by providing a loop with anterior and posterior strap sections according to the disclosure unevenly distributing pressure. The shoulder-immobilizer embodiments facilitate easy and intuitive donning and doffing, e.g., by a clinician donning the device on a user on an operating room bed or by a user donning the shoulder brace one-handed at home during recovery.

C. Embodiments of the Arm Apparatus

Embodiments of the disclosure depict an arm apparatus suitable, but unnecessary, for the shoulder immobilizer embodiments described above. The shoulder immobilizer and arm apparatus may be used together to immobilize a shoulder and provide for flexibility of arm motion; in alternative embodiments, the shoulder immobilizer embodiments described above may be used without the arm apparatus embodiments, and vice versa.

To ease understanding of the disclosed embodiments of a shoulder immobilizer and arm apparatus, the front or anterior, and rear or posterior portions of the shoulder immobilizer and arm apparatus are described independently. The anterior and posterior portions of the shoulder immobilizer and arm apparatus function together to form a shoulder immobilizer that encompasses the user's anatomical portions.

Figure 11:
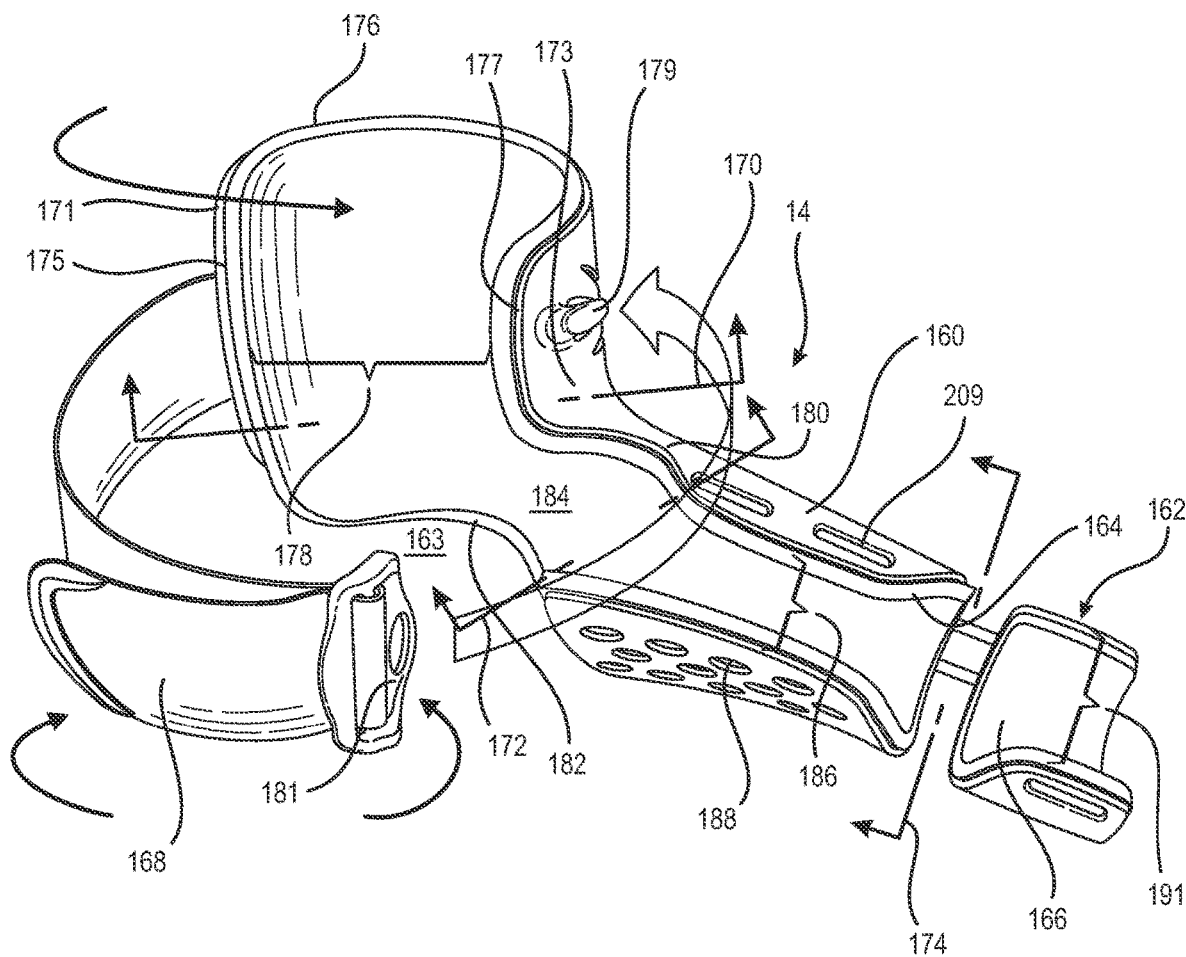
FIG. 11 is a perspective view of an embodiment of the arm apparatus of FIG. 1.

FIG. 11 illustrates an embodiment of an arm apparatus 14. The arm apparatus 14 comprises a main body 160 defining an upper arm region 170, an elbow region 172, and a forearm region 174. The elbow region 172 forms an opening 163 between the upper arm region 170 and the forearm region 174 for permitting elbow extension, as shown in FIGS. 17A and 17B. The arm apparatus 14 also includes a hand support or extension 162 attached to the forearm region 174 and adapted to support a user's hand. The arm apparatus 14 further includes a liner 164 preferably extending along an inner surface of the main body 160, and an extension liner 166 extending along an inner surface of the hand extension 162.

The main body 160 forms different regions to accommodate a user's arm and position it according to different protocols. The forearm region 174 generally extends perpendicularly relative to the upper arm region 170 and maintains a user's arm, particularly the elbow's articulation for the user. The upper arm region 170 forms an upper arm contour having a generally semi-circular profile 176 to ergonomically arrest a user's arm. The upper arm region 170 preferably forms a posterior flange 171 and/or anterior flange 173 opposite the posterior flange 171 and extending along at least part of the semi-circular profile 176.

An upper arm strap 168 may extend from and engage the posterior flange 171 and the anterior flange 173. The upper arm strap 168 combined with the posterior and anterior flanges 171, 173 generally forms a complete circumferential loop with the semi-circular profile 176 to retain the upper arm within the upper arm region 170.

Although there may be different ways to arrange the upper arm strap 168, it is intended to facilitate attachment and detachment of the upper arm strap 168 with a single hand. For example, the anterior flange 173 may define a retainer 179 extending therefrom. The upper arm strap 168 has an attachment such as a clip 181 arranged to removably engage the retainer 179, as exemplified by the arrow in FIG. 11. The posterior flange 171 forms a posterior edge 175 and the anterior flange 173 forms an anterior edge 177. A clearance 178 is defined between the posterior and anterior edges 175, 177. The clearance 178 extends generally on a lateral side of the arm apparatus 14 to permit easy entry and removal of the upper arm from the arm apparatus 14. The upper arm strap 168, preferably extends between the posterior and anterior flanges 171, 173. The length of the upper arm strap 168 may be adjusted at the clip 181 based on the arm apparatus 14 and/or the user's dimensions.

As depicted, the upper arm strap 168 may include first and second strap segments 192, 194 having first ends connecting to the upper arm region 170 at different locations on the posterior side of the upper arm region 170 and connecting to singularly connect to the anterior side of the upper arm region 170. By singularly connecting, the upper arm strap 168 may extend over a broad area of the upper arm region 170 and across the clearance 178 while still permitting single-handed manipulation of the upper arm strap 168.

Figure 15:
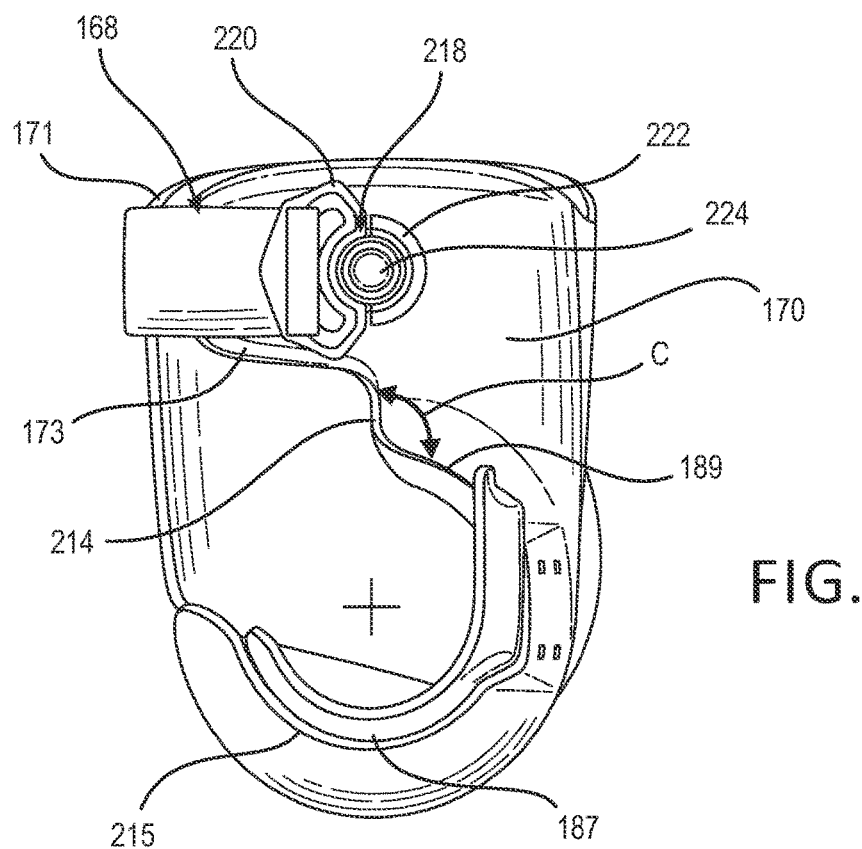
FIG. 15 is a front elevational view of the arm apparatus of FIG. 11.
Figure 16:
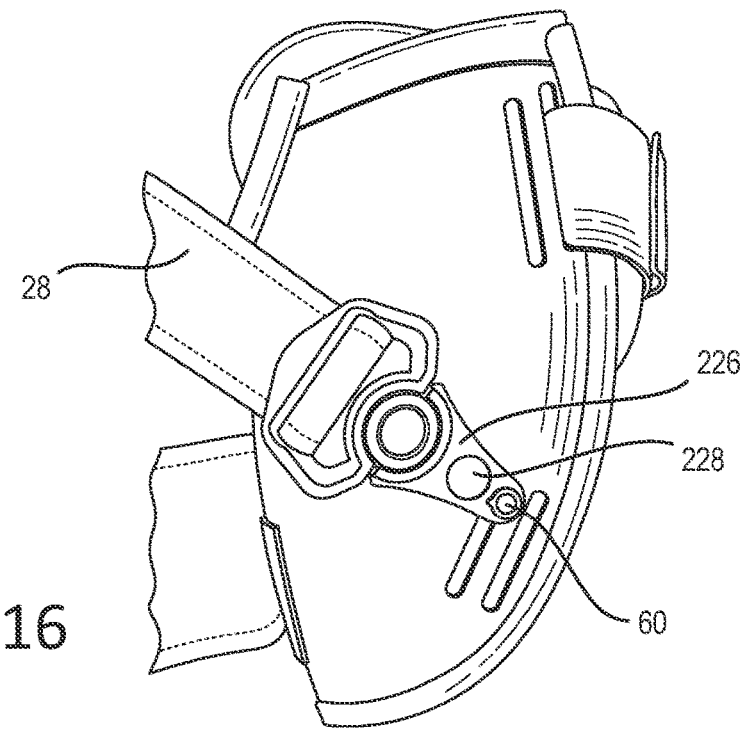
FIG. 16 is a rear elevational view of the arm apparatus of FIG. 11.

In a variation in FIG. 15, a coupling device 218 is connected to the upper arm region 170 and arranged to removably couple the upper arm strap 168 to the anterior portion of the upper arm region 170, permitting attachment and detachment by a single hand. The coupling device 218 preferably includes a clip 220 connecting to the upper arm strap 168 by a button 224 engaging a frame 222.

A retainer 226 rotatably connects the posterior strap 28 to a mount 60 by a keyhole connection 228. The retainer 226 is preferably on the upper arm region 170 proximate a user's triceps. This arrangement offers angular freedom. The line of pull of the posterior strap 28 is directly from the olecranon straight through the axis of the humerus, which is physiologically impossible, thereby achieving shoulder tension and/or immobilization. With different torso heights, the posterior strap 28 has its angle of pull adjusted and offers the additional benefit of repeatable tension since the user need not undo the strap adjustment for cleaning.

To facilitate allowing the user's arm to go from flexion, such as in the configuration of the arm apparatus 14, or extension to straighten the elbow, as depicted in FIGS. 17A and 17B, the main body 160 may define an upper notch 180 along a periphery thereof generally opposite the opening 163. The upper notch 180 is located preferably proximate a junction of the upper arm region 170, the elbow region 172, and the forearm region 174. The main body 160 may define a lower notch 182 generally opposite the opening 163. The lower notch 182 may be located proximate a junction of the upper arm region 170, the elbow region 172, and the forearm region 174 likewise. The upper and lower notches 180, 182 form part of the elbow opening 184 along with the clearance 178, permitting articulation of an elbow relative to the main body 160. This advantageously allows for greater flexibility and compliance by a user during everyday life, as the user is enabled to extend the arm through the elbow as needed.

Figure 12:
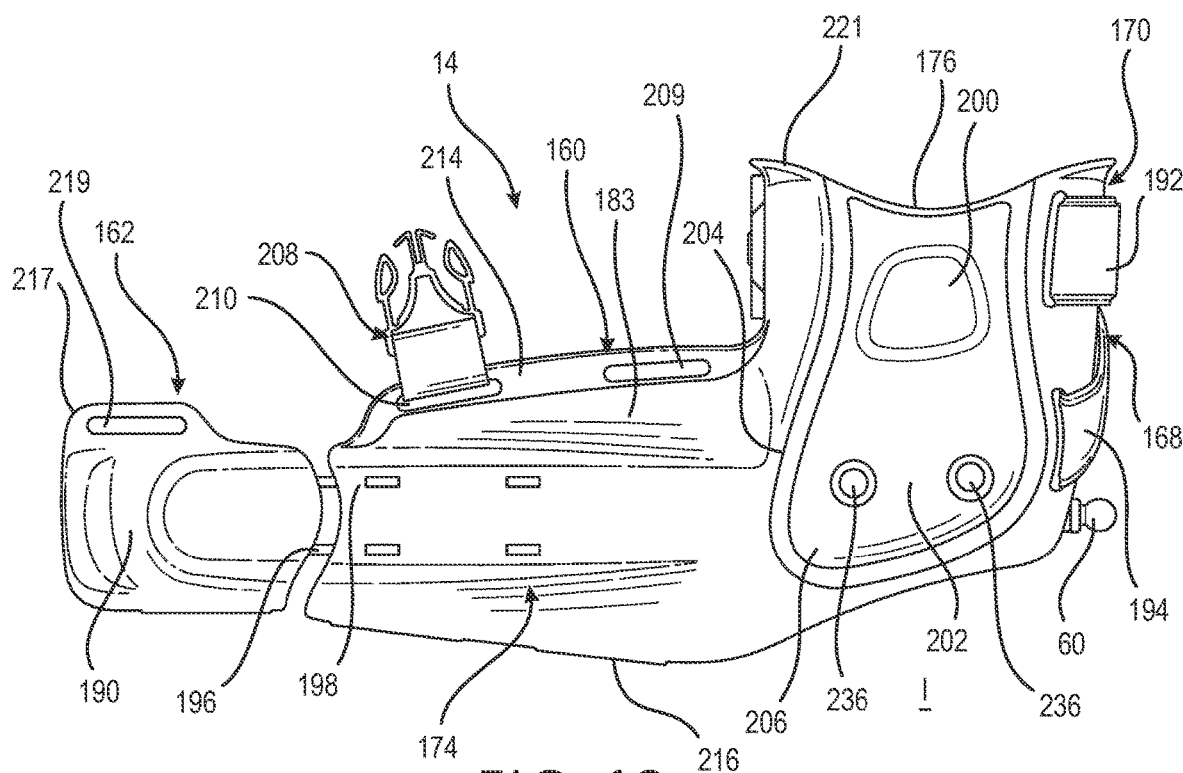
FIG. 12 is a first side elevational view of the arm apparatus of FIG. 11.

FIG. 12 shows an inside surface I of the arm apparatus 14, intended to face toward a user. The upper arm region 170 may define an inward contour 200 toward or proximal to the upper arm contour 176 extending into or toward the opening 163 along an outer surface 201 of the main body 160. The inward contour 200 may be provided to ergonomically contour inwardly to offload a humeral region of the arm. The upper arm region 170 defines a bulbous outer contour 202 inferior relative to the upper arm contour 176 and extending away from the opening 163. The bulbous outer contour 202 may be arranged to provide a clearance for the medial humeral epicondyle. The upper arm region 170 also defines a recess 204 arranged to receive a liner 206 with padding or compressible properties adapted to press or be arranged adjacent to the arm. The upper arm region 170 defines rolled edges 221 flaring from the upper arm contour 176 to distribute pressure on a user's arm better and avoid sharp contact.

The upper arm region 170 may include fastener attachments 236 that protrude therefrom and are arranged to engage the fasteners 150, 152 of the sheath 142, or another connector to the shoulder immobilizer 11. In some embodiment variations, the fastener attachments 236 may be apertures defined in a thickness of the main body 160.

Figure 13:
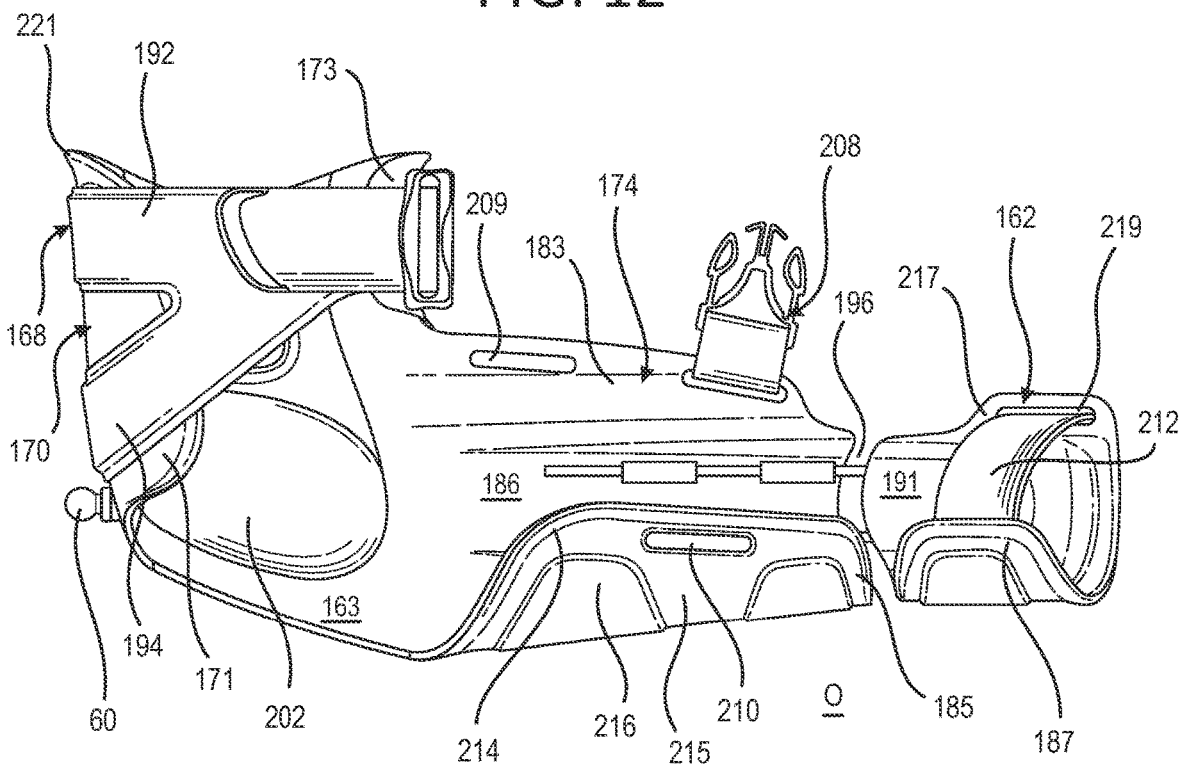
FIG. 13 is a second side elevational view of the arm apparatus of FIG. 11.

FIG. 13 shows an outside view O of the arm apparatus 14, configured to face away from a user. The forearm region 174 forms opposed first and second peripheral edges 183, 185 subtending an elongate lateral clearance 186. The first and second peripheral edges 183, 185 are configured to wrap about a user's forearm and prevent departure therefrom while still allowing the user to move the elbow into extension by removing the forearm through the lateral clearance 186. The first and second peripheral edges 183, 185 may each form a rolled edge 214 defined as departing from a contour of a main portion 189 of the main body 160 at a predetermined angle C. The predetermined angle C may generally depart from an arcuate contour of the forearm region 174 bounded between the peripheral edges 183, 185.

The peripheral edges 183, 185 may likewise each form or define a slot 209, 210, preferably within the rolled edge 214. The at least one slot 209, 210 is adapted to receive a strap extending across the lateral clearance 186 to enclose and secure the forearm, for example circumferentially. The strap may include a fastener 208, which may be configured to be replaceable between the slots 209, 210 depending on the user's dimensions and rehabilitation needs.

The main body 160 may define a plurality of openings 188 extending therethrough. The main body 160 is preferably formed from a rigid or semi-rigid material, and the openings 188 enable a better transfer of air through the arm apparatus 14. The openings 188 may also be sized and located to strategically reduce weight—and a cost—of the arm apparatus 14 without sacrificing needed rigidity and support. Preferably, the liner 164 is likewise breathable and combined with the openings 188 allows for comfortable breathability of the arm apparatus 14.

The extension 162 is preferably slidably secured to a distal end of the forearm region 174 to permit length adjustment depending on the length of a user's arm. The extension 162 defines a sidewall 190 and a supporting portion 187 having an arcuate profile and extending from the sidewall 190 to bear the weight of a user's hand. An upper clearance 191 is subtended by peripheral edges of the sidewall 190 and the supporting portion 187.

The sidewall 190 preferably forms a rolled edge 217 that may correspond to the rolled edge 214 of the forearm region 174. The rolled edge 217 preferably defines a slot 219. A strap assembly 212 may be attached to the extension 162 and extends across the upper clearance 191 and through the slot 219 thereby forming a circumferential engagement with the user's hand.

As shown in FIG. 17, a liner 230 may be arranged to extend along the inner surface 193 of the extension 162. The liner 230 may define an elongate portion 234 and a bulbous portion 232 adapted to a hand or palm of a hand.

Figure 14A:
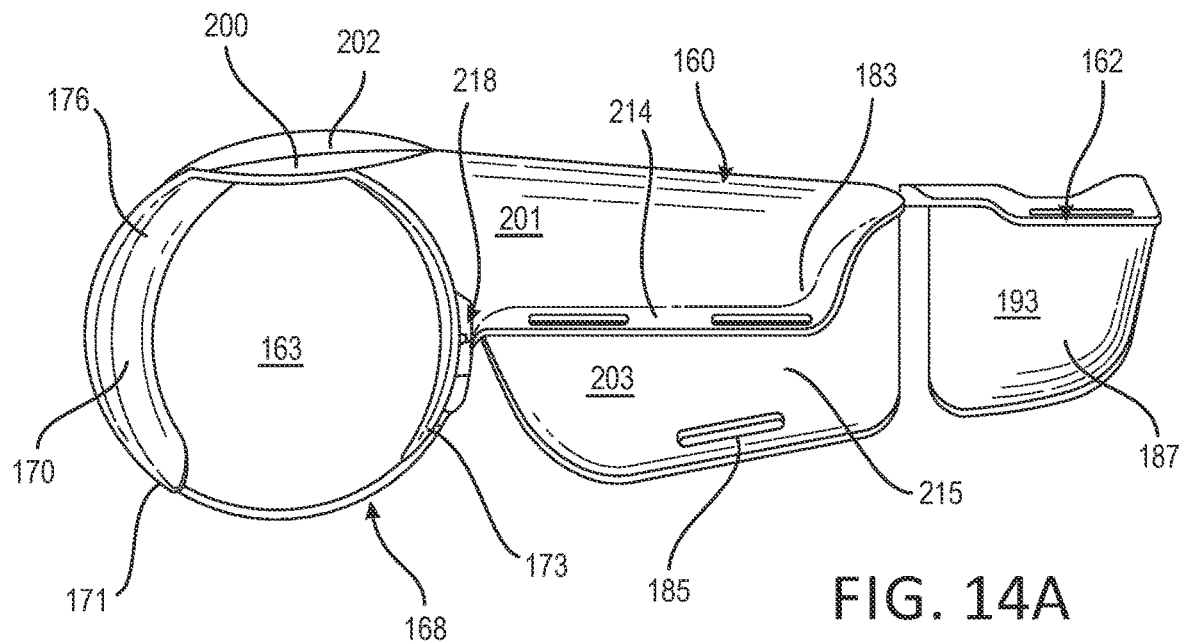
FIG. 14A is a top plan view of the arm apparatus of FIG. 11.

As shown in FIG. 14A, the forearm region 174 defines a supporting portion 215 corresponding in shape continuously with the supporting portion 187 of the extension 162 to provide for even resting and support of a user's arm and corresponding hand. The supporting portions 187, 215 having inner surfaces 193, 203, respectively, extend continuously relative to one another as if there is no gap between the forearm region 174 and the extension 162.

The extension 162 may be slidably mounted to the forearm region 174 of the main body 160 by a bar 196 and channel 198 arrangement. The extension 162 preferably defines a rolled edge 217 that may correspond to the rolled edge 214 of the forearm region 174.

To accommodate different arm sizes, the forearm region 174 includes malleable stays 216 along the supporting portion 215. These malleable stays 216 may be formed from aluminum or other material allowing manipulation to reside in a shape and custom fit to a user's anatomy. The malleable stays 216 preferably have enough resiliency and strength to allow the main body 160 to deform and maintain the deformation of a base material of the main body 160. While shown as extending laterally relative to the lateral clearance 186, the malleable stays 216 may be formed from a plurality of orientations. The malleable stays 216 may be within a thickness of the main body 160 or may be attached to a surface of the main body 160. In such an embodiment, the malleable stays 216 may be removed as desired (for example to reduce weight of the arm apparatus 14), or additional malleable stays or stays, such as rigid, having different properties may be added, all depending on the user's particular dimensions and needs.

The overall sizing and curvature of the arm apparatus 14 is a one-size-fits-all brace. The main body 160 has the malleable stays 216, and the materials forming the main body 160 are preferably rigid to support the heaviest of forearms without a circumferential strap. The upper arm region 170 may likewise have malleable stays, but do not require the same strength/rigidity requirements. For example, the upper arm region 170 may comprise a thin injection molded plastic so the upper arm strap 168 about a user's bicep can offer the structure.

Figure 14B:
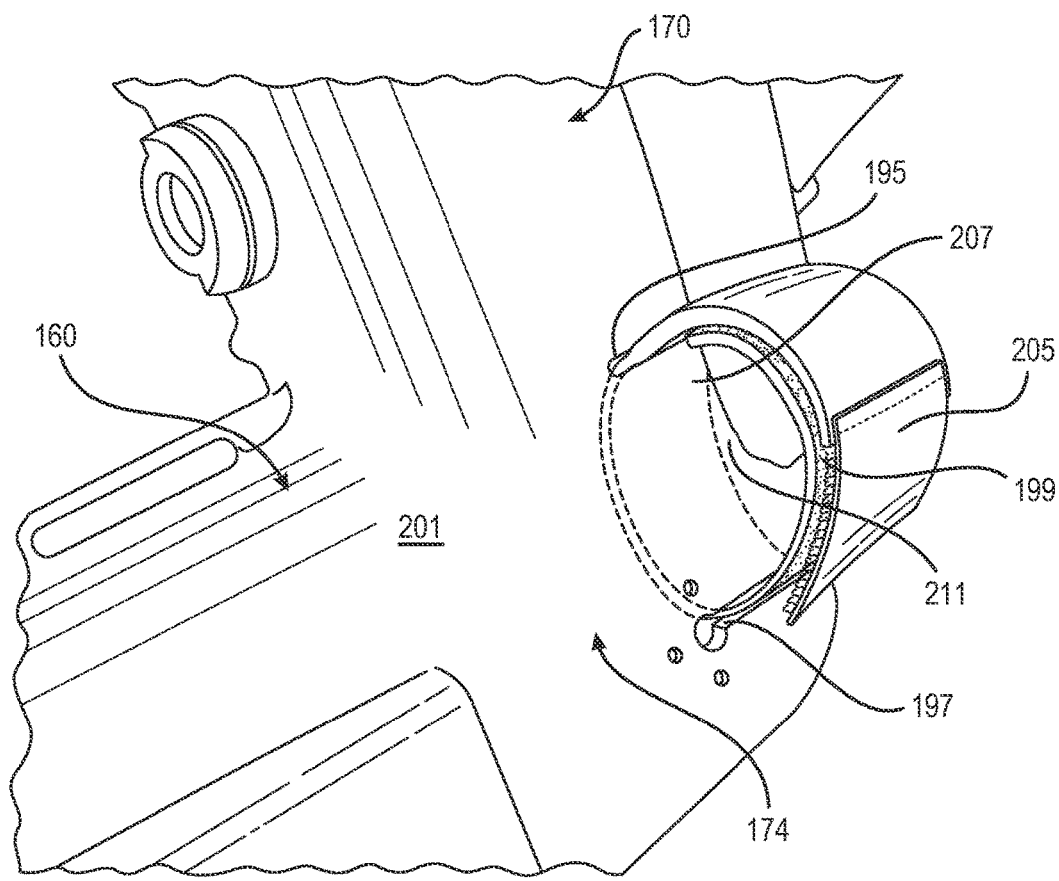
FIG. 14B is a perspective view of the arm apparatus of FIG. 11.

FIG. 14B shows an alternative embodiment in which the arm apparatus 14 may be attached to the shoulder immobilizer 11. A strap 199 is configured to loop through a channel 207 defined in a thickness of the main body 160 of the arm apparatus 14. The channel 207 may be accessed via slots 195, 197. The strap 199 may comprise a fastener 205 comprising, for example, hook material configured to contact loop material defined on a surface of the strap 199. A strap 22, 24 of the shoulder immobilizer 11 may be engaged by the loop 211 by threading the strap 22, 24 through the loop 211 or by forming the loop 211 around the strap 22, 24. This arrangement allows the arm apparatus 14 to be removable attached to the shoulder immobilizer 11 in a releasable, intuitive, and simple manner.

According to embodiments disclosed, the arm apparatus disclosed advantageously provide improved support that allows for greater flexibility of use. The arm apparatus is compatible with shoulder immobilizer embodiments disclosed and provides enhanced support to a user's upper arm, elbow, and forearm while also allowing for the extension of the elbow, for example for improved participation in daily activities or for more comfortable sleep.

The shoulder immobilizer and arm apparatus embodiments of the disclosure further address existing shoulder brace solutions being difficult and counter-intuitive to use, uncomfortable, and not lending themselves to daily activities.

The invention claimed is:

1. A shoulder immobilizer adapted to immobilize a shoulder of a user and to connect to an arm apparatus, comprising:
   a first portion defining a loop adapted to extend about a contralateral shoulder;
   a second portion including a first belt adapted to extend along an anterior side of the user from a first end of the first portion, and a second belt adapted to extend along a posterior side of the user from a second end of the first portion, the first and second belts arranged for connecting to one another, the first and second belts arranged to couple to one another on an anterior side of the user;
   wherein the second portion is arranged to secure to the arm apparatus;
   wherein the first portion comprises first and second segments forming said loop;
   wherein the first and second segments join at an inferior junction adapted to be positioned at a location proximate a contralateral elbow;
   wherein the first portion and the first belt forms a first "figure-9" strap configuration arranged to extend in the loop about the contralateral shoulder from the inferior junction superiorly over an anterior portion of the contralateral shoulder and about a posterior portion of the contralateral shoulder inferiorly directed to the first belt directed about an anterior side of the user.

2. The shoulder immobilizer of claim 1, wherein the first and second belts extend from the second and first segments, respectively, and are arranged at an oblique angle relative to one another.

3. The shoulder immobilizer of claim 1, wherein the first and second segments extend and intersect through a pad generally located about the inferior junction.

4. The shoulder immobilizer of claim 1, wherein the first and second belts extend from the inferior junction at generally a same height.

5. The shoulder immobilizer of claim 1, wherein the second segment is adapted to be arranged relative to the first belt about the contralateral shoulder when the shoulder immobilizer is tensioned such that a third force superiorly exerted by the second segment counteracts a second force inferiorly exerted by the first belt about the contralateral shoulder.

6. The shoulder immobilizer of claim 5, wherein the first segment is adapted to be arranged relative to the second belt about the contralateral shoulder when the shoulder immobilizer is tensioned such that a first force superiorly exerted by the first segment counteracts a fourth force inferiorly exerted by the second belt about the contralateral shoulder.

7. The shoulder immobilizer of claim 6, wherein the first force extends obliquely opposite to the third force.

8. The shoulder immobilizer of claim 6, wherein the second force extends obliquely opposite to the fourth force.

9. The shoulder immobilizer of claim 1, wherein the second portion further comprises an anterior strap attachable to the first segment and arranged to secure to the arm apparatus.

10. The shoulder immobilizer of claim 9, wherein the anterior strap attaches to the first segment at a location superior of the inferior junction.

11. The shoulder immobilizer of claim 10, wherein the anterior strap includes a first strap portion connecting to the second segment by a first height adjuster and to the arm apparatus by a connector, the anterior strap having a second strap portion extending from the connector and detachably securing to the first strap portion to adjust a length of the anterior strap.

12. The shoulder immobilizer of claim 11, wherein the second portion further comprises a posterior strap attachable to the second segment and arranged to secure to the arm apparatus;
   wherein the posterior strap attaches to the second segment at a location superior of the inferior junction.

13. The shoulder immobilizer of claim 12, further comprising a posterior panel connecting the second belt to the posterior strap;
   wherein the posterior panel is a flexible textile extending between the second belt and the posterior strap.

14. The shoulder immobilizer of claim 13, wherein the posterior panel is a plate having rigid or semi-rigid properties;
   wherein the second belt slidably extends through the plate through at least one retainer or slot.

15. The shoulder immobilizer of claim 14, wherein the posterior strap slidably extends through the plate through the at least one retainer or slot;
   wherein the plate has a profile adapted to extend along a spine of the user.

16. The shoulder immobilizer of claim 11, wherein the first height adjuster includes a slider connected to the first segment and a coupler slidably engaging the slider, the coupler engaging the anterior strap.

17. The shoulder immobilizer of claim 1, further comprising:
   the arm apparatus including a main body defining an upper arm region, an elbow region and a forearm region, the elbow region having an opening located between the upper arm region and the forearm region.

18. The shoulder immobilizer of claim 17, wherein the arm apparatus includes an extension attached to the forearm region.

19. The shoulder immobilizer of claim 17, wherein the forearm region generally extends perpendicularly relative to the upper arm region.

20. The shoulder immobilizer of claim 17, wherein the upper arm region defines a generally semi-circular profile, the upper arm region forming a posterior flange and/or and anterior flange extending along at least part of the generally semi-circular profile.

* * * * *